(12) United States Patent
Daniels et al.

(10) Patent No.: US 7,854,737 B2
(45) Date of Patent: Dec. 21, 2010

(54) INSTRUMENT AND ASSOCIATED METHOD OF TRAILING FOR MODULAR HIP STEMS

(75) Inventors: David W. Daniels, Warsaw, IN (US); Kimberly A. Dwyer, Fort Wayne, IN (US); David A. Mattingly, Weston, MA (US)

(73) Assignee: Depuy Products, Inc., Warsaw, IN (US)

( * ) Notice: Subject to any disclaimer, the term of this patent is extended or adjusted under 35 U.S.C. 154(b) by 493 days.

(21) Appl. No.: 10/327,527

(22) Filed: Dec. 20, 2002

(65) Prior Publication Data

US 2004/0122440 A1 Jun. 24, 2004

(51) Int. Cl.
*A61B 17/56* (2006.01)
*A61F 2/44* (2006.01)

(52) U.S. Cl. .................... 606/102; 623/20.35
(58) Field of Classification Search ............... 606/102, 606/79, 80, 84, 85, 86, 87, 89; 623/20.35, 623/20.36, 22.15, 22.4, 22.41–22.46, 23.11, 623/23.14, 23.15, 23.21–23.24, 23.31, 23.34, 623/23.35, 23.42, 23.44, 23.46, 23.47
See application file for complete search history.

(56) References Cited

U.S. PATENT DOCUMENTS

| | | | |
|---|---|---|---|
| 2,492,249 A | | 12/1949 | Willard et al. |
| 3,067,740 A | | 12/1962 | Haboush |
| 3,271,868 A | | 9/1966 | Kuntscher et al. |
| 3,801,989 A | | 4/1974 | Mckee |
| 3,810,312 A | | 5/1974 | Carson |
| 4,051,559 A | * | 10/1977 | Pifferi ..................... 623/22.46 |
| 4,131,998 A | | 1/1979 | Spears |
| 4,335,715 A | | 6/1982 | Kirkley |
| 4,517,969 A | | 5/1985 | Halcomb et al. |
| 4,608,055 A | | 8/1986 | Morrey |
| 4,658,808 A | * | 4/1987 | Link ..................... 623/16.11 |
| 4,676,797 A | | 6/1987 | Anapliotis et al. |
| 4,716,894 A | | 1/1988 | Lazzeri et al. |
| 4,917,530 A | | 4/1990 | Engelhardt et al. |
| 4,938,762 A | | 7/1990 | Wehrli |
| 4,959,066 A | | 9/1990 | Dunn et al. |
| 4,969,911 A | | 11/1990 | Greene |
| 5,002,578 A | * | 3/1991 | Luman ..................... 623/22.42 |

(Continued)

FOREIGN PATENT DOCUMENTS

AU 2003266447 11/2003

(Continued)

OTHER PUBLICATIONS

European Search Report for Eurpoean Application No. 03257810.6-2310, dated Apr. 5, 2004 2 pages.

(Continued)

*Primary Examiner*—Todd E Mahahan
*Assistant Examiner*—David Comstock

(57) ABSTRACT

A trial (100) for use in performing joint arthroplasty is provided. The trial (100) fits to a cavity (103) in the canal (105) of a long bone (107) and assists in the performing of a trial reduction in performing joint arthroplasty. The trial (100) includes a stem portion (102) and a neck portion (104) fixedly connected to the stem portion (102) in a plurality of selectable positions with respect to the stem portion (102).

8 Claims, 35 Drawing Sheets

U.S. PATENT DOCUMENTS

| | | | |
|---|---|---|---|
| 5,002,581 A | 3/1991 | Paxson et al. | |
| 5,064,427 A | 11/1991 | Burkinshaw | |
| 5,100,407 A | 3/1992 | Conrad et al. | |
| 5,133,760 A | 7/1992 | Petersen et al. | |
| 5,135,529 A | 8/1992 | Paxson et al. | |
| 5,197,989 A | 3/1993 | Hinckfuss et al. | |
| 5,201,882 A | 4/1993 | Paxson | |
| 5,314,492 A * | 5/1994 | Hamilton et al. | 623/23.34 |
| 5,364,401 A | 11/1994 | Ferrante et al. | |
| 5,370,706 A | 12/1994 | Bolesky et al. | |
| 5,476,466 A | 12/1995 | Barrette et al. | |
| 5,507,824 A | 4/1996 | Lennox | |
| 5,507,830 A | 4/1996 | DeMane et al. | |
| 5,514,136 A | 5/1996 | Richelsoph | |
| 5,601,567 A | 2/1997 | Swajger et al. | |
| 5,607,431 A | 3/1997 | Dudasik et al. | |
| 5,645,607 A | 7/1997 | Hickey | |
| 5,653,765 A * | 8/1997 | McTighe et al. | 623/22.42 |
| 5,658,349 A | 8/1997 | Brooks et al. | |
| 5,674,225 A | 10/1997 | Muller | |
| 5,700,268 A | 12/1997 | Bertin | |
| 5,725,592 A * | 3/1998 | White et al. | 623/23.35 |
| 5,728,128 A | 3/1998 | Crickenberger et al. | |
| 5,766,261 A | 6/1998 | Neal et al. | |
| 5,776,200 A | 7/1998 | Johnson et al. | |
| 5,792,143 A | 8/1998 | Samuelson et al. | |
| 5,810,829 A | 9/1998 | Elliott et al. | |
| 5,810,830 A | 9/1998 | Noble et al. | |
| 5,824,068 A | 10/1998 | Bugge | |
| 5,849,015 A | 12/1998 | Haywood et al. | |
| 5,858,020 A | 1/1999 | Johnson et al. | |
| 5,860,969 A | 1/1999 | White et al. | |
| 5,876,459 A | 3/1999 | Powell | |
| 5,879,391 A | 3/1999 | Slamin | |
| 5,885,299 A | 3/1999 | Winslow et al. | |
| 5,888,245 A | 3/1999 | Meulink et al. | |
| 5,902,339 A | 5/1999 | Keller | |
| 5,906,644 A | 5/1999 | Powell | |
| 5,919,195 A | 7/1999 | Wilson et al. | |
| 5,935,172 A | 8/1999 | Ochoa et al. | |
| 5,951,564 A | 9/1999 | Schroder et al. | |
| 5,951,606 A | 9/1999 | Burke | |
| 5,976,147 A | 11/1999 | LaSalle et al. | |
| 5,976,188 A | 11/1999 | Dextradeur et al. | |
| 5,989,259 A | 11/1999 | Penenberg et al. | |
| 5,993,455 A | 11/1999 | Noble | |
| 6,027,507 A | 2/2000 | Anderson et al. | |
| 6,045,556 A | 4/2000 | Cohen | |
| 6,071,311 A | 6/2000 | O'Neil et al. | |
| 6,080,162 A | 6/2000 | Dye et al. | |
| 6,097,978 A | 8/2000 | Demarais et al. | |
| 6,102,950 A | 8/2000 | Vaccaro | |
| 6,102,956 A | 8/2000 | Kranz | |
| 6,110,179 A | 8/2000 | Flivik et al. | |
| 6,113,605 A | 9/2000 | Storer | |
| 6,117,138 A | 9/2000 | Burrows et al. | |
| 6,126,694 A | 10/2000 | Gray, Jr. | |
| 6,136,035 A * | 10/2000 | Lob et al. | 623/23.15 |
| 6,165,177 A | 12/2000 | Wilson et al. | |
| 6,179,877 B1 | 1/2001 | Burke | |
| 6,193,724 B1 | 2/2001 | Chan | |
| 6,193,759 B1 | 2/2001 | Rio et al. | |
| 6,197,065 B1 | 3/2001 | Martin et al. | |
| 6,206,884 B1 | 3/2001 | Masini | |
| 6,224,605 B1 | 5/2001 | Anderson et al. | |
| 6,238,435 B1 | 5/2001 | Meulink et al. | |
| 6,258,095 B1 | 7/2001 | Lombardo et al. | |
| 6,258,097 B1 | 7/2001 | Cook et al. | |
| 6,277,123 B1 | 8/2001 | Maroney et al. | |
| 6,319,286 B1 | 11/2001 | Fernandez et al. | |
| 6,330,845 B1 | 12/2001 | Meulink | |
| 6,332,886 B1 | 12/2001 | Green et al. | |
| 6,355,068 B1 | 3/2002 | Doubler et al. | |
| 6,361,563 B2 | 3/2002 | Terrill-Grisoni et al. | |
| 6,432,110 B1 | 8/2002 | Richelsoph | |
| 7,235,106 B2 | 6/2007 | Daniels et al. | |
| 2001/0001121 A1 | 5/2001 | Lombardo et al. | |
| 2001/0007957 A1 | 7/2001 | Martin et al. | |
| 2001/0053935 A1 | 12/2001 | Hartdegen | |
| 2007/0244566 A1 | 10/2007 | Daniels et al. | |

FOREIGN PATENT DOCUMENTS

| | | |
|---|---|---|
| EP | 0381893 A1 | 8/1990 |
| EP | 0381893 B1 | 8/1990 |
| EP | 0677821 A2 | 12/1994 |
| EP | 0 824 013 A1 | 2/1998 |
| EP | 1 004 283 A2 | 5/2000 |
| EP | 1004283 A3 | 5/2000 |
| EP | 1022001 A | 7/2000 |
| EP | 1099427 B1 | 11/2000 |
| EP | 1 234 558 A2 | 8/2002 |
| EP | 1234558 A3 | 8/2002 |
| EP | 1437103 A2 | 12/2002 |
| FR | 2416002 | 8/1979 |
| FR | 2492249 | 4/1982 |
| FR | 2684287 A1 | 4/1993 |
| FR | 2705558 A1 | 5/1993 |
| FR | 2 705 558 A1 | 12/1994 |
| FR | 2735971 A1 | 6/1995 |
| JP | 2004202234 | 7/2004 |
| WO | WO 96/15739 | 5/1996 |
| WO | WO 0217826 A | 3/2002 |

OTHER PUBLICATIONS

European Search Report for Eurpoean Application No. 03257813.0-2310, dated May 11, 2004, 2 pages.

European Search Report for Eurpoean Application No. 03257816.3-2210, dated May 18, 2004, 2 pages.

Zimmer brochure entitled "ZMR Revision taper Hip Prosthesis"; Copyright 1999 Zimmer, inc. 26 pages.

AcuMatch brochure entitled "AcuMatch M-Series Modular Femoral Stem, Operative Technique Draft"; Copyright 2001 Exactech, Inc.; 14 pages.

Stryker brochure entitled "Restoration Modular Revision System, Surgical Protocol"; for purposes of this patent application only, this Stryker brochure depicts a prosthetic device publicly available at least as earlier as Dec. 19, 2002; 22 pages.

Biomet brochure entitled "Mallory-Head Modular Calcar, Modular Calcar Revision System"; for purposes of this patent application only, this Biomet brochure depicts a prosthetic device publicly available at least as earlier as Dec. 19, 2002, 20 pages.

Link brochure entitled: "Surgical Technique with the MP Hip Stem for Revision of a Failed Femoral Hip Stem"; for purposes of this patent application only, this Link brochure depicts a prosthetic device publicly available at least as earlier as Dec. 19, 2002, 12 pages.

* cited by examiner

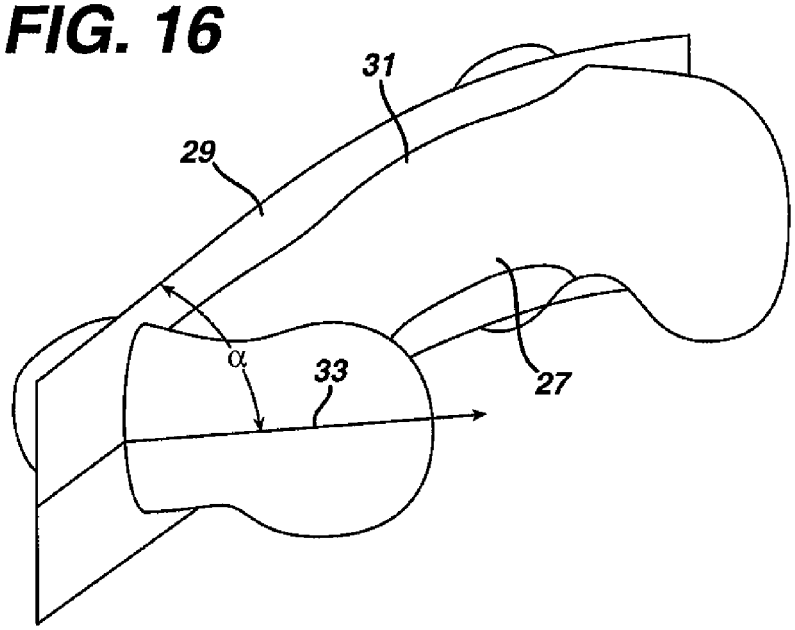
FIG. 16
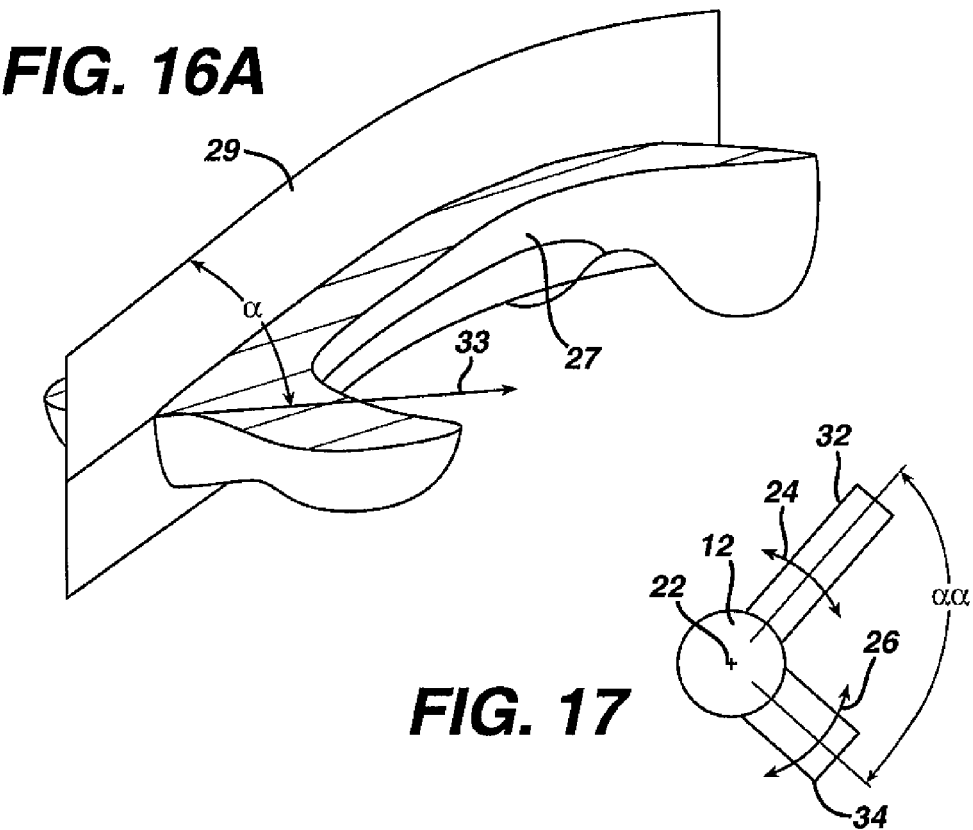
FIG. 16A
FIG. 17

INSTRUMENT AND ASSOCIATED METHOD OF TRAILING FOR MODULAR HIP STEMS

CROSS-REFERENCE TO RELATED APPLICATIONS

Cross reference is made to the following applications: U.S. patent application Ser. No. 10/327,187 entitled "ADJUSTABLE BIOMECHANICAL TEMPLATING & RESECTION INSTRUMENT AND ASSOCIATED METHOD", U.S. Pat. No. 7,022,141 entitled "ALIGNMENT DEVICE FOR MODULAR IMPLANTS AND METHOD", and U.S. Pat. No. 7,235,106 entitled "MODULAR HIP STEMS AND ASSOCIATED METHOD OF TRIALING" filed concurrently herewith which are incorporated herein by reference.

TECHNICAL FIELD OF THE INVENTION

The present invention relates generally to the field of orthopedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

Currently in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck offsets, head offsets and leg lengths. The combination of these four factors affects the laxity of the soft tissue. By optimizing the biomechanics, the surgeon can provide a patient a stable hip much more resistant to dislocation. In order to accommodate the range of patient arthropometrics, a wide range of hip implant geometries are currently manufactured by DePuy Orthopedics, Inc., the assignee of the current application, and by other companies. In particular, the S-ROM® total hip systems offered by DePuy Orthopaedics, Inc. include three offsets, three neck lengths, four head lengths and one leg length adjustment. The combination of all these biomechanic options is rather complex.

Anteversion of a total hip system is closely linked to the stability of the joint. Improper version can lead to dislocation and patient dissatisfaction. Version control is important in all hip stems. However, it is a more challenging issue with the advent of stems with additional modularity.

The prior art has provided for some addressing of the anteversion problem. For example, the current S-ROM® stems have laser markings on the medial stem and the proximal sleeve. This marking enables the surgeon to measure relative alignment between these components. Since the sleeve has infinite anteversion, it is not necessarily oriented relative to a bony landmark that can be used to define anteversion. In fact, the current sleeves are sometimes oriented with the spout pointing directly laterally into the remaining available bone.

Prior art stems may be aligned relative to a patient's bony landmarks. These stems are monolithic. They cannot locate the neck independently of the distal stem. Therefore, the anteversion is limited. Most bowed, monolithic stems are sold in fixed anteversion; for example, at an anteversion of 15 degrees. These monolithic stems have limited flexibility for rotational alignment since the distal stem must follow the bow of the patient's femur and this may not provide an operable biomechanical result.

In a common step in the surgical procedure known as total hip arthroplasty, a trial or substitute stem is first implanted into the patient. The trial is utilized to verify the selected size and shape of the implant in situ on the patient and the patient is subjected to what is known as a trial reduction. This trial reduction represents moving the joint, including the trial implant through selected typical motions for that joint. Current hip instruments provide a series of trials of different sizes to help the surgeon assess the fit and position of the implant. Trials, which are also known as provisionals, allow the surgeon to perform a trial reduction to assess the suitability of the implant and implant's stability prior to final implant selection. In order to reduce inventory costs and complexity, many trialing systems are modular. For example, in the Excel Instrument System, a product of DePuy Orthopaedics, Inc., there is a series of broaches and a series of neck trials that can be mixed and matched to represent the full range of implants. There is a single fixed relationship between a broach and a neck trial, because these trials represent a system of monolithic stem implants.

Likewise, in the current S-ROM® instrument systems provided by DePuy Orthopaedics, Inc., there are neck trials, proximal body trials, distal stem trials, head trials and sleeve trials. By combining all these components, the implant is represented. Since the S-ROM stem is modular and includes a stem and a sleeve, the angular relationship or relative anteversion between the neck and the sleeve is independent and represented by teeth mating between the neck and the proximal body trial. The proximal body trial has fixed transverse bolts that are keyed to the sleeve in the trialing for straight, primary stems. The long stem trials do not have the transverse bolts and are thus not rotationally stable during trial reduction and therefore are not always used by the surgeon.

With the introduction of additional implant modularity, the need for independent positioning of the distal stem, proximal body and any sleeve which comprise the implants is required. Currently bowed, monolithic stems are offered with a fixed amount of anteversion, typically 15 degrees.

Thus, a need for a prosthetic trial and related implants that provide for anteversion alignment relative to a patient's bony landmark exists.

SUMMARY OF THE INVENTION

Accurate trialing of stem implants is particularly critical with difficult revision cases. Specifically, since the final axial position of the distal stem implant is often unknown and not identical to the axial placement of the distal stem trial, a final check with a trial is an advantage to a surgeon. Although this can be done in some current systems, it has not been shown with mechanical key ways that improve the accuracy of the alignment. According to the present invention, a trial and related surgical method is provided with key ways, teeth, grooves, etc. to provide a mechanical means of communicating mechanically alignment information which is considerably more accurate than the standard method of laser marking and visual recreation. The implant trials of the present invention allow for accurate measurement and mapping of the rotational position of all components within the trial.

In modular prosthetic stem designs, bowed stems follow the anatomical curve of the intermedullary canal of the long bone, and by having a modular stem design, the surgeon is now able to optimize the rotational position of all three components. Thus, infinite anteversion of the proximal body implant is possible even when used with bowed distal stems. In addition to standard instrument requirements such as reproducing range of implant sizes and shapes, the present invention describes a trial and a surgical procedure with additional features that are critical to the functionality of a modular stem implant. These new requirements include accurate mapping of the relative alignment of neck trials, proximal body trials, distal stem trials and sleeve trials to their corresponding implant components. The requirements also include providing absolute alignment relative to the intramedullary canal and to provide alignment using mechanical features in addition to standard techniques using laser markings. Further, the new implant requirements include a new trialing design which is compatible with existing implants which clearly expands the value of the new design trial.

The trial of the present invention provides for absolute anteversion in a bowed revision stem. The surgeon may simply use a bowed distal stem trial to locate the anterior bow of the femur. By utilizing this bowed distal stem trial, the bowed intramedullary canal can be used to define anteversion anatomically, and the absolute anteversion of a patient's bone in situ can be dimensioned using these tools of the present invention. With the present invention, the bowed intramedullary canal of the femur can be used to define anteversion anatomically.

In one aspect, the present invention provides a trial for use in performing joint arthroplasty. The trial is to be fitted to a cavity in the canal of a long bone. The trial comprises a stem portion and a neck portion. The neck portion is fixedly connected to the stem portion in a plurality of selectable positions with respect to the stem portion.

In another aspect, the present invention provides a kit for use in performing joint arthroplasty. The kit comprises a trial and an implant. The trial is for use in performing joint arthroplasty. The trial is to be fitted to a cavity in the canal of a long bone and to assist in performing a trial reduction in performing joint arthroplasty. The trial includes a stem portion and a neck portion selectively operably connected to said portion in a plurality of selectable positions with respect to the stem portion. The implant is for use in performing joint arthroplasty. The implant is to be fitted to a cavity in the canal of a long bone and to assist in performing joint arthroplasty. The implant includes a stem portion and a proximal body portion selectively operably connected to the stem portion in a plurality of selectable positions with respect to the stem portion.

In another aspect, the present invention provides a trial for use in performing total hip arthroplasty. The trial is to be fitted to a cavity in the femoral canal of a femur and is provided to assist in performing a trial reduction in performing joint arthroplasty. The trial comprises a stem portion and a neck portion. The stem portion defines a longitudinal axis. The neck portion is selectively rotatably connected to the stem portion and fixedly connectable in plurality of selectable positions with respect to the stem portion about the longitudinal axis of the stem portion.

In another aspect, the present invention provides a kit for use in performing hip joint arthroplasty. The kit comprises a trial and an implant set. The trial is for use in performing joint arthroplasty; the trial is to be fitted to a cavity in the canal of a long bone and to assist in performing a trial reduction in performing joint arthroplasty. The trial includes a stem portion and a neck portion selectively operably connected to the stem portion in a plurality of selectable positions with respect to the stem portion. The implant set includes a plurality of proximal bodies and distal components. An implantable implant is to be selected from one of the proximal bodies and one of the distal components. The implantable implant is to be positioned in the cavity of the long bone, so that the proximal body and the distal component can be assembled to form a hip femoral component assembly without the removal of the distal component from the cavity and so that the implantable implant can be assembled from said implant set.

In another aspect, the present invention provides a method for providing joint arthroplasty. A long bone is resected. A cavity is prepared in the medullary canal of the long bone. A trial is provided. The trial has a stem portion and a neck portion adjustably, fixedly connected to the stem portion in a plurality of selectable positions with respect to the stem portion. The stem portion has a feature to cooperate with a bony landmark of the patient. One of a plurality of selected positions is selected. A trial reduction is performed using the trial. The optimum position of the neck portion with respect to the stem portion is determined. An implant is selected with the optimum position of the neck portion with respect to the stem portion. An implant is selected with the optimum position of the neck portion with respect to the stem portion. A selected implant is implanted in the cavity.

In another aspect, the present invention provides a method for providing joint arthroplasty comprising resecting a long bone and preparing a cavity in the medullary canal of the long bone. A trial is provided having at least two portions; the two portions are rotatable with respect to one another. An implant is provided having at least two portions; the two portions are rotatable with respect to one another. A tool is also provided. The tool, the portions of the trial and the portions of the implant have mating keys and keyways for determining the relative rotational position of said portions of said trial and said implant.

In another aspect, the present invention provides a method for providing joint arthroplasty wherein the joint includes a long bone having a bow and a neck and an intramedullary canal having a bow. The method comprises determining the position of a plane through the bow and intramedullary canal of the long bone and determining the anatomic anteversion angle from the position of the plane of the bow and the position of the neck. A trial is provided having a stem portion and a neck portion adjustably, fixedly connected to the stem portion in a plurality of selectable positions with respect to the stem portion. The stem portion has a bow to fit in the bow of the intramedullary canal. The neck portion is positioned on the stem portion at a trial anteversion angle based upon the anatomic anteversion angle. An implant is provided having a stem portion and a proximal portion adjustably, fixedly connected to the stem portion in a plurality of selectable positions with respect to the stem portion. The stem portion has a bow to fit the bow in the intramedullary canal. The proximal portion of the implant is positioned on the stem portion of the implant at a prosthetic anteversion angle based upon the trial anteversion angle.

The technical advantages the present invention include the ability of the trials of the present invention to be used such that a distal stem implant may be placed in situ and the proximal body trial and neck trial be placed on the distal stem implant. This combination of distal stem implant and proximal body trial may be accomplished without damaging the locking taper on the distal stem implant or to require the removal of the distal stem implant. For example, according to one aspect of the present invention, the trial includes a distal stem trial and a proximal body trial. The proximal body trial can be used with both the distal stem trial and the distal stem implant, and trialing of the proximal portion can be accomplished with the distal stem implant in situ. Thus, the present invention provides for mixing of components which are trial components of the present invention and implant components.

The technical advantages of the present invention further include the ability of the trial of the present invention to provide absolute and relative rotational alignment of all components including the proximal body, distal stem, neck and the sleeve. Rotational alignment can be based on the position of the stem in the intramedullary canal of the long bone.

The technical advantages of the present invention further include the ability to translate the rotational position of the distal stem as far proximal as possible. For example, according to one aspect of the present invention, the proximal body trial is keyed to the distal stem. Thus, the present invention permits the position of the proximal body of the trial to be a substitute for the relative position of the distal stem trial or implant.

The technical advantage of the present inventions also include the ability of either the trial sleeve or the implant sleeve to have infinite rotation. For example, according to one aspect of the present invention, the sleeve is fitted with an internal taper over an external taper on the proximal body of the trial or implant. The connection between the proximal body trial and a sleeve is a slip fit. The connection between the proximal body implant and a sleeve is a taper lock. Thus, the present invention provides for the proximal body trial to have an absolute angular measurement of this sleeve for accurate alignment of the stem in the intramedullary canal and to the neck axis.

The technical advantage of the present invention further includes the ability to align the implant or trial either on the back table or in situ in the patient. For example, according to one aspect of the present invention, the surgical technique provides for an instrument to be used with the implant and the trial such that the proper orientation of the implant can be determined based upon the discovered and fine-tuned position of the trial found in situ on the patient or through CT scans, radiographs, or other imaging techniques. Thus, the present invention provides for a surgical technique that allows rotational alignment to be mapped from instruments to implants either on the back table or in the bone.

Another technical advantage of the present invention is that the angular position can be dialed or determined by use of a cervix coupling or teeth which may be rotated with a click type feel every, for example, ten degrees. For example, according to one aspect of the present invention, the trial includes mating gears which form a cervix coupling between the proximal body trial and the neck trial to assist in determining the relative position of the neck to the distal stem. Thus, the present invention provides simple anteversion adjustment without the need to view any marks on the prosthesis.

The technical advantages of the present invention further includes the additional safety of a combination of a threaded engagement and a tapered fit for the implants. For example, according to one aspect of the present invention, the trials of the present invention, provide for a slip fit between the distal stem and the proximal body trial and a nut contained within the neck trial which may be engaged with an external thread on the proximal end of the distal stem. Thus, the present invention provides for two well proven forms of connections to provide for a secure connection of the proximal body and neck to the distal stem.

A further technical advantage of the present invention includes a quick connect option to improve the ergonomics and provide immediate feedback on leg length prior to trial reduction. For example, according to one aspect of the present invention, the proximal body includes a spring type clip to hold the proximal body in position against the distal stem without any nuts or locked tapered engagement. Thus, the present invention provides for a quick connect option to improve ergonomics and provide immediate feedback on leg length prior to trial reduction.

A further technical advantage of the present invention is the ability of the trials of the present invention to be compatible with monolithic stems as well as with modular stems. Thus, for example according to one aspect of the present invention, the trials may be sized to match with existing monolithic implants as well as with modular prosthesis. The use of the trials that work with modular as well as with monolithic implants minimizes complexity of the instrumentation, duplication, and reduces the quantity of inventory required. For example, according to one aspect of the present invention, the implant of the present invention may work for both monolithic and modular prosthesis. Thus, the present invention provides for a trial that works with both monolithic and modular stem implants.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 16 is a perspective view of a femur, from the proximal end of the femur, illustrating a plane through the bow of the femur;

FIG. 16A is a cross-section of the femur of FIG. 16;

FIG. 17 is a top view of the stem of FIG. 12;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
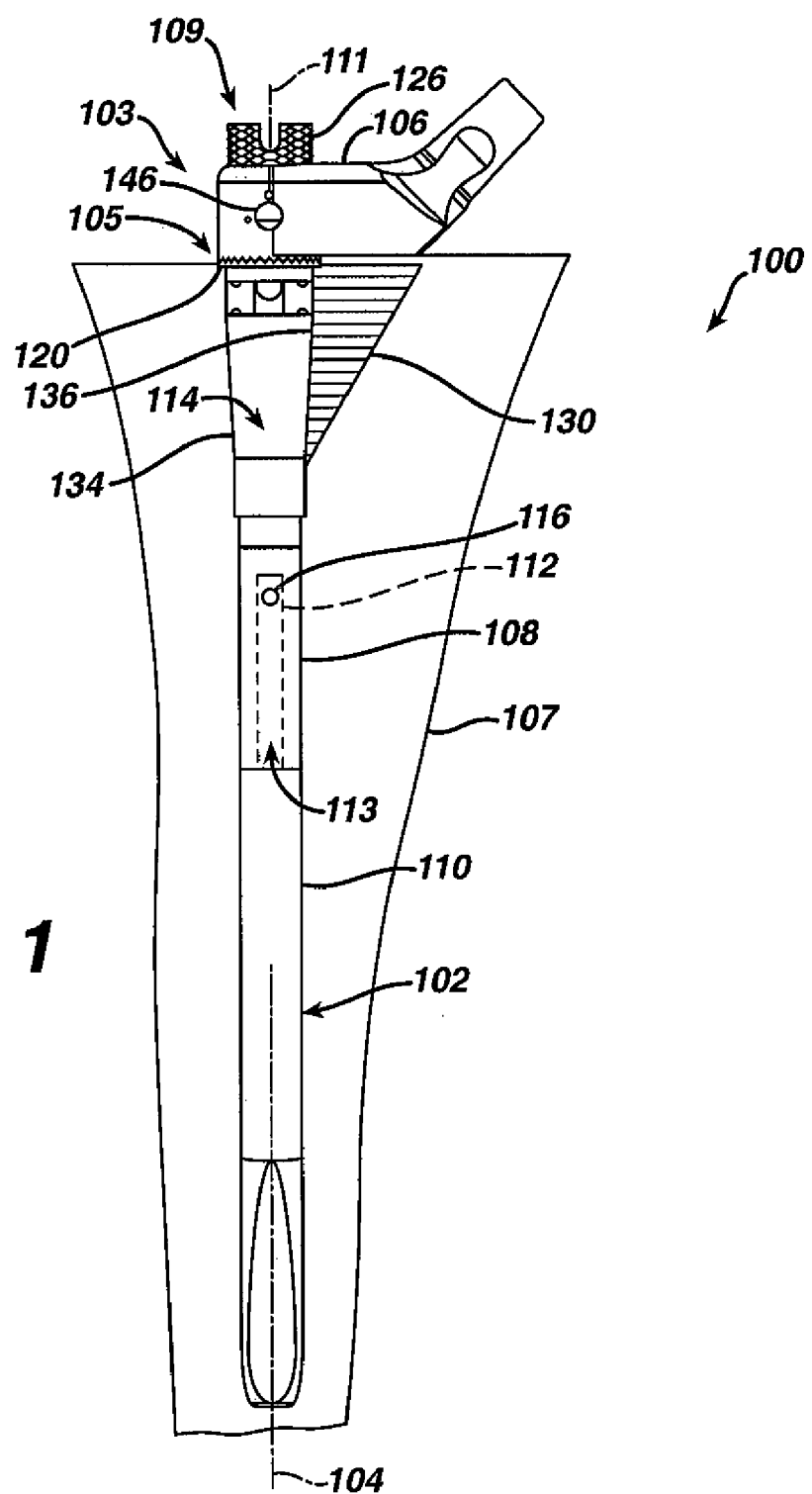
FIG. 1 is a plan view of a modular trial in accordance with an embodiment of the present invention.

Referring now to FIG. 1, a trial 100 is shown for use in arthroplasty. Often orthopedic surgeons utilize trials such as the trial 100 to place a substitute prosthetic item in the patient's body that can be removed after the trialing or prior to the final selection of the prosthesis. Once the dimensions of the trial are verified through reduction or movements of the patient's leg through the typical motion that a patient will require, the trial is removed and is sterilized for later use in other surgeries. Conversely, a prosthetic implant, once exposed to a patient, is not utilized again. Therefore, it is important the shape, position and location of the appropriate trial be exactly duplicated by the actual implant. The trial 100 is utilized for performing joint arthroplasty. The trial 100 is adapted to be fitted to a cavity 103 in the canal 105 of a long bone 107. The trial 100 is utilized to assist in performing a trial reduction for joint arthroplasty. The trial 100 includes a stem portion 102 and a proximal body portion 114 fixedly connected to the stem portion 102 in a plurality of selectable positions with respect to the stem portion 102.

The stem portion 102 may define a longitudinal axis 104 of the stem portion 102. The neck portion 106 defines an opening 109 therein. The opening 109 defines a longitudinal axis 111 of the neck portion 106 and the proximal body portion 114. The longitudinal axis 111 of the opening 109 is preferably coincident with the longitudinal axis 104 of the stem portion 102. The neck portion 106 is rotatably connected to the proximal body 114 about the longitudinal axis 104 of the stem portion 102.

The distal stem assembly 102 may include a proximal stem portion 108, which is connected to a curved distal stem portion 110. The proximal stem portion 108 and the curved distal stem portion 110 may be integral or, as shown in FIG. 1, the curved distal stem portion 110 may include a protrusion 112 which mates with a cavity 113 in the proximal stem portion 108. A pin 116 may be used to connect the proximal stem portion 108 to the curved distal stem portion 110.

Figure 4:
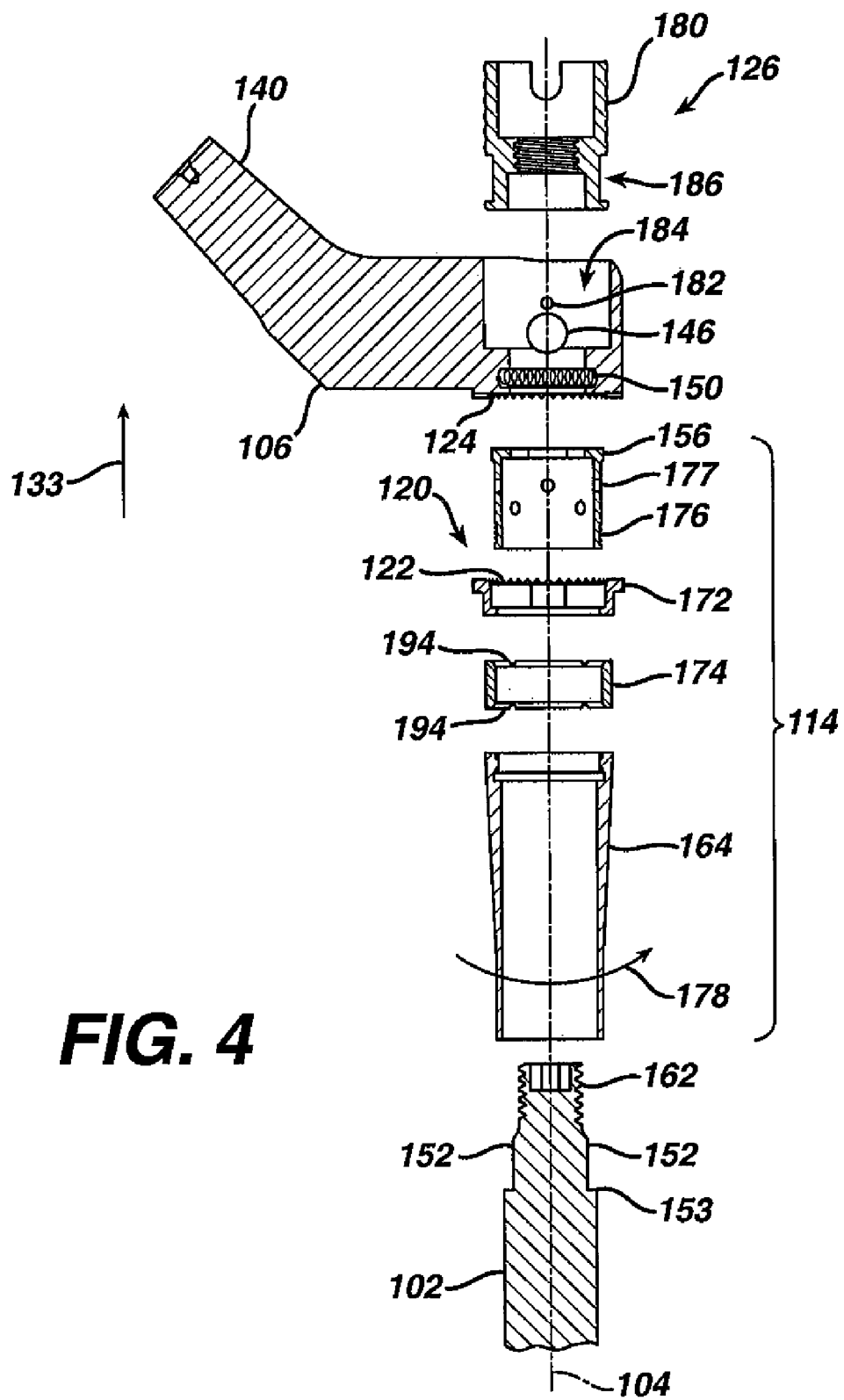
FIG. 4 is a partial exploded cross-sectional view of the modular trial of FIG. 1.

Referring now to FIGS. 2 through 10, preferably the neck trial 106 is connected to the distal stem assembly 102 in such a way that the angular position along centerline 104 between the neck trial and the distal stem may be adjusted. For example, as shown in FIGS. 2 through 10, the proximal body trial 164 may include an index mechanism 120 that permits a fixed degree of rotational adjustment between the neck trial 106 and the distal stem assembly 102. Referring to FIGS. 4 through 8, the index mechanism 120 may include first gear or spline 122. The index mechanism 120 may also include a second spline or gear 124 which meshes in and out selectively of engaging with the first gear 122. The second spline or gear 124 may, as shown in FIG. 4, be integral with the neck trial 106. It should be appreciated that optionally the second gear 124 may be a separable component fixably secured to the proximal body 106. The gears 122 and 124 each have a plurality of teeth 136. Each tooth is substantially the same as all other teeth 136. The teeth 136 of each of the gears 122 and 124 are virtually the same. The teeth 136 are spaced equally radially around the centerline 104 of the stem. When the teeth 136 of, for example, the first gear 122 are rotated one (1) tooth respect to the second gear 124, the first gear 122 is rotated by relationship which comprises: 1 divided by the number of teeth on a gear, times 360 degrees.

Thus, for a first gear 122 and a second gear 124, each having 36 teeth, the single index of the first gear 124 provides for a 10 degree relative motion of the first gear 122 with respect to the second gear 124. As shown in FIG. 4, when the first gear 122 is moved in the direction of arrows 133 toward the second gear 124, the gears 122 and 124 may be locked into engagement. Similarly, when the first gear 122 and the second gear 124 are moved away from each other in the opposite direction of arrows 133, the neck trial 106 is permitted to rotate with respect to the stem 102. Thus, the index mechanism 120 may provide for 36 different relative positions to the neck trial 106 with respect to the distal stem assembly 102 when the gears 122 and 124 each contain 36 teeth.

Figure 4A:
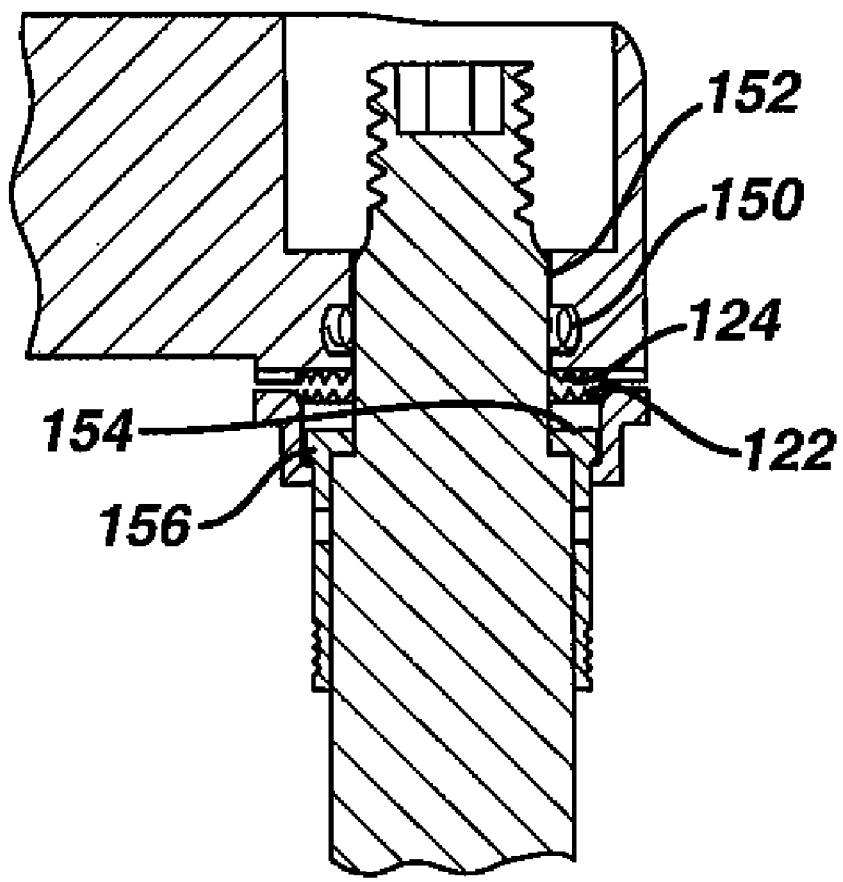
FIG. 4A is a partial exploded cross-sectional view of the modular trial of FIG. 1 showing the index mechanism in greater detail.

Any of a variety of mechanisms may be used to engage and disengage the gears or splines 122 and 124 with each other. Preferably, and as shown in FIGS. 4 and 4(a), the gears or splines 122 and 124 are selectively engaged and disengaged by means of a spring 150 which is used to gently urge the first gear 122 into engagement with the second gear 124. When the stem 102 is placed in position in the neck trial 106, the stem 102 includes a circular rib 152 which when the stem 102 is fully engaged into the neck trial sandwiches the spring 150, the first gear 122 and the second gear 124, and the proximal body trial 114 between the rib 152 and an annular shoulder 153 on the stem 102 which mates with nut 158.

Preferably, the location of the rib 152 and the shape and size of the spring 150 are designed such that the spring 150 is sufficient to gently engage the first gear 122 in mesh with the second gear 124. The spring 152, however, is weak enough to permit the gentle indexing of the neck trial 106 relative to the stem 102 to provide easy adjustment of the anteversion angle. Once the proper anteversion angle has been determined, the neck trial 106 needs to be firmly and securely engaged with the stem 102.

Figure 5:
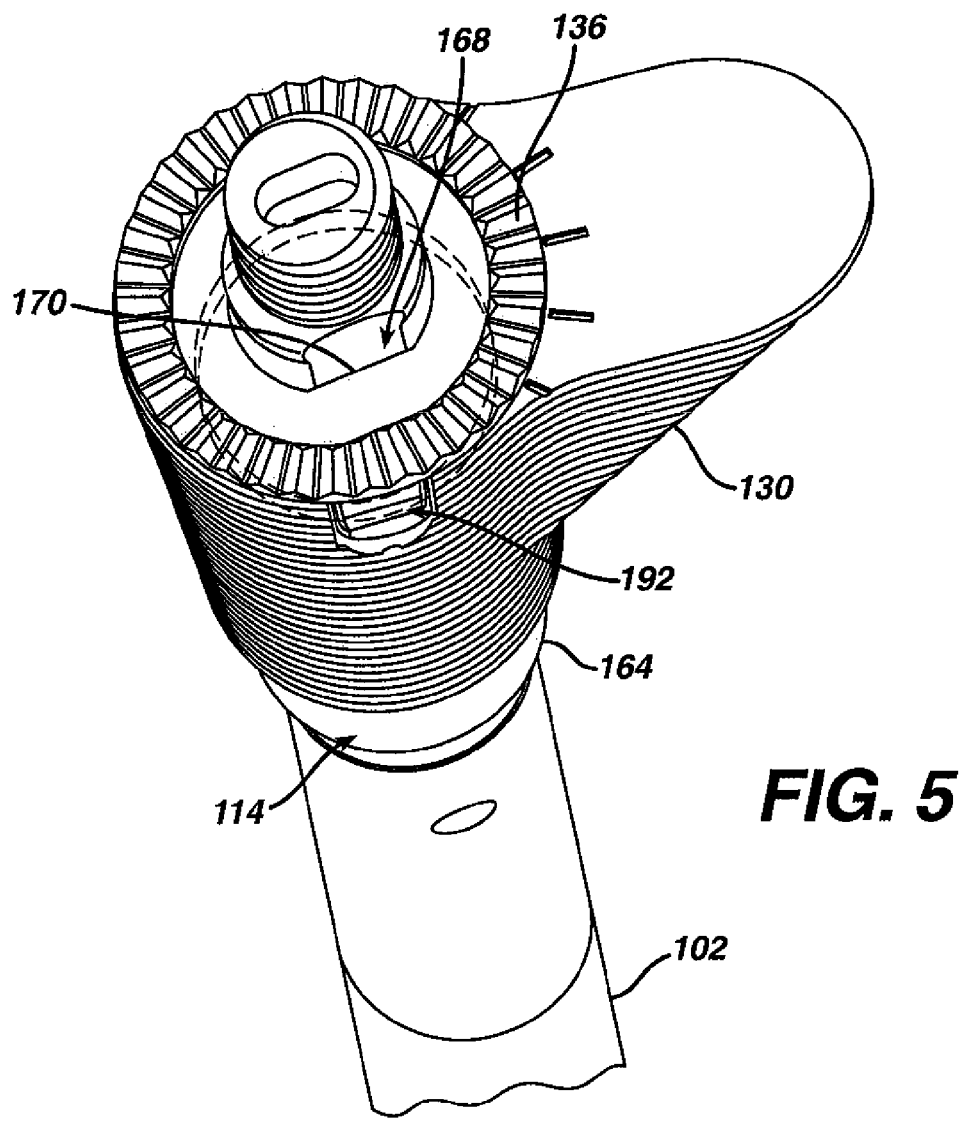
FIG. 5 is a partial perspective view of proximal portion of the modular trial of FIG. 1.

Preferably, and as shown in FIG. 4, the proximal end of the stem 102 includes external threads 162 that engage with connector nut 126. Referring to FIGS. 4 and 5, the trial 100 may include the proximal body trial 114, which is comprised of a sleeve 164 that slidably fits over the stem 102. The proximal end of the sleeve 164 includes internal threads 166 that mate with external threads 176 on the keyed component 156. As shown in FIG. 5, the keyed component 156 has a central opening 168 with opposed flats 170. Similarly, the keyed component 156 has a second timing feature (not shown) that cooperates with a location feature (not shown) on the spline member. The location features on the keyed component 156 and the first gear 122 cooperate to permit the first gear 122 to move axially in the direction of centerline 104 but prevent rotation of the first gear 122 with respect to the keyed component 156. A ring 174 is slidably fitted over the outer diameter 177 of the keyed component 156. The ring 174 is permitted to freely rotate with respect to the spline member 172 and the keyed component 156. The keyed component 156 is assembled by threadably engaging into the sleeve 164 causing the spline member 172 and ring 174 to be trapped there between.

Although the keyed member 156, spline member 172, ring 174 and sleeve 164 can be supplied to the surgeon as individual components, they can also be preassembled before being supplied to the surgeon, thereby saving the surgeon the time of assembling these components in the operating room. The assembly of the keyed member 156, spline member 172, ring 174 and sleeve 164 is designated the proximal body portion 114 in the drawings and in this description.

Figure 6:
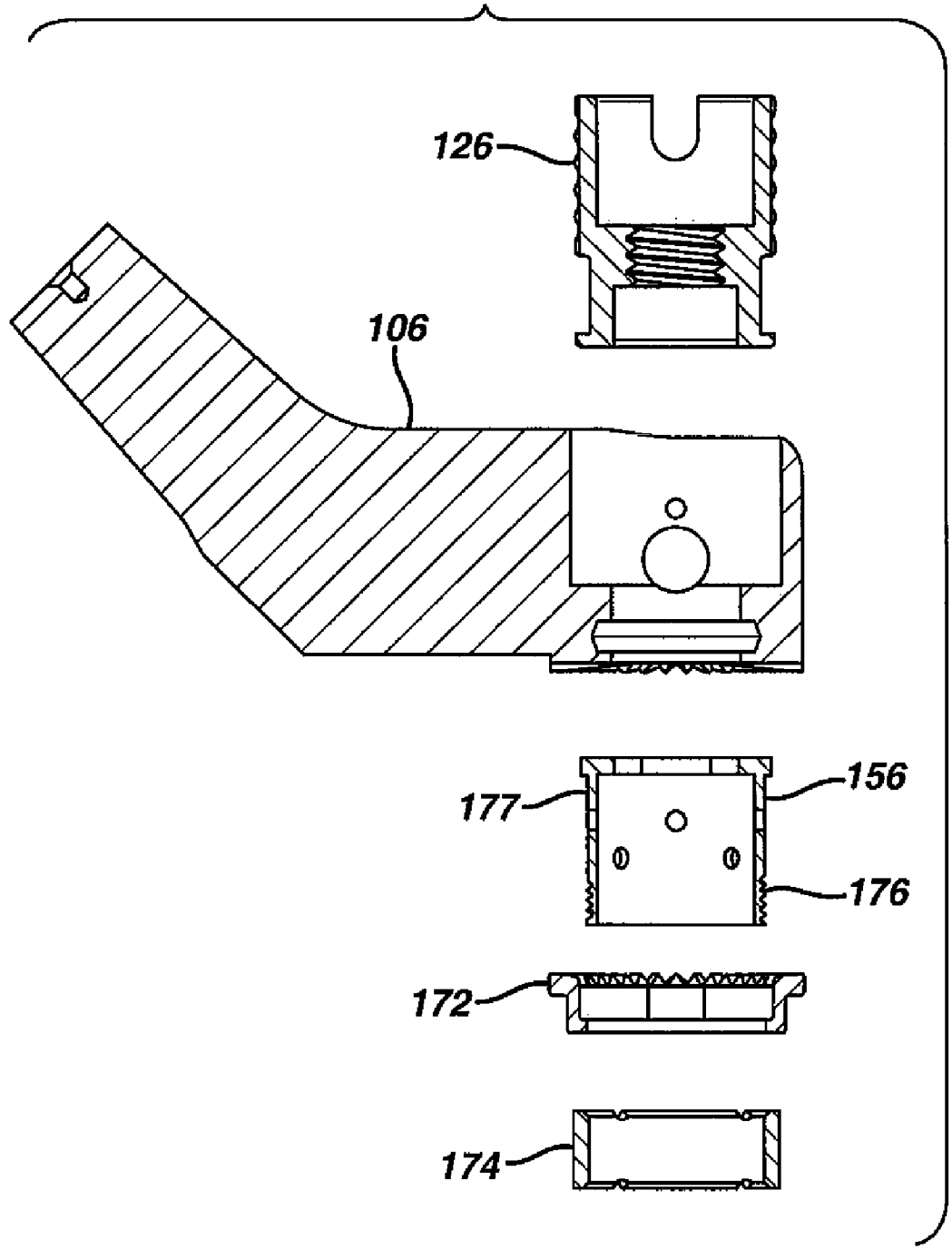
FIG. 6 is a partial cross-sectional plan view of the modular trial of FIG. 1.
Figure 7:
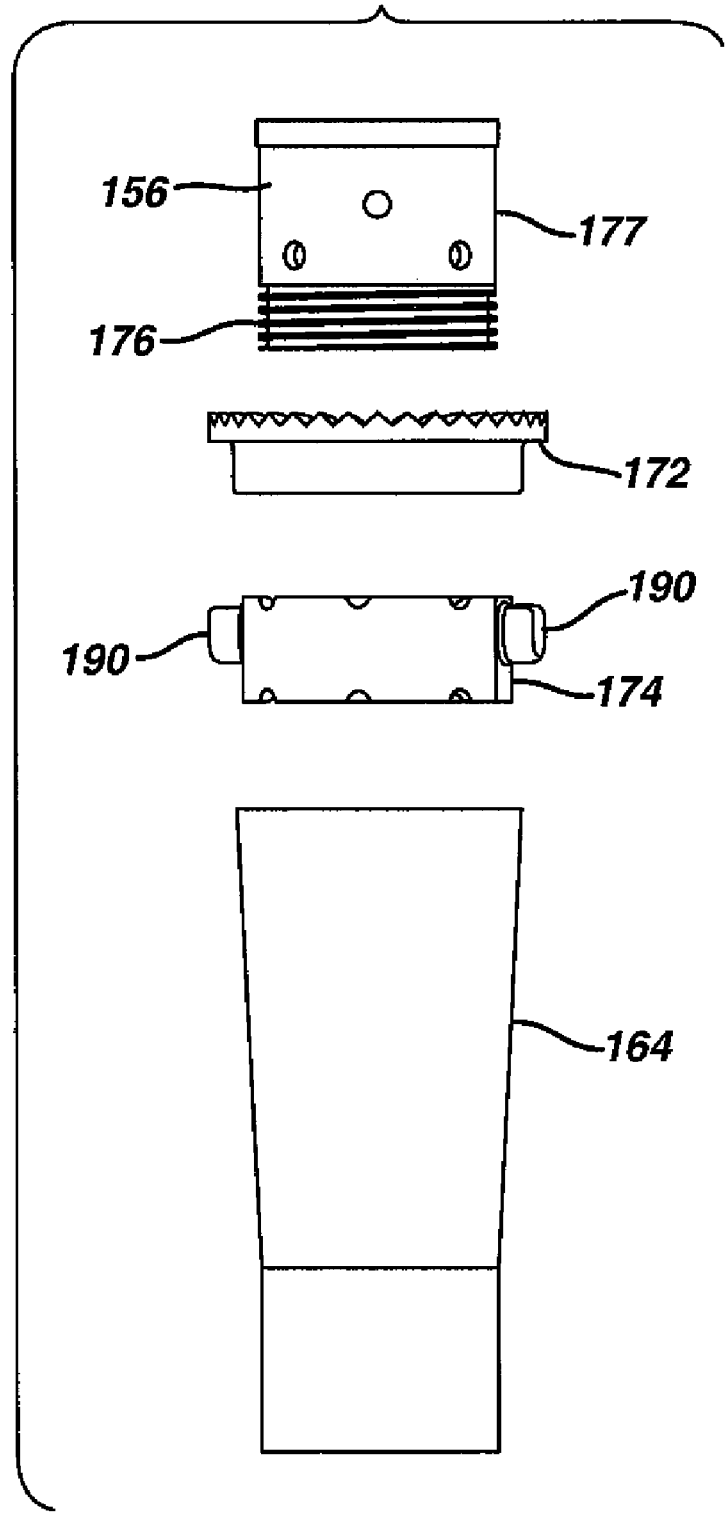
FIG. 7 is a partial plan view of the modular trial of FIG. 1.
Figure 8:
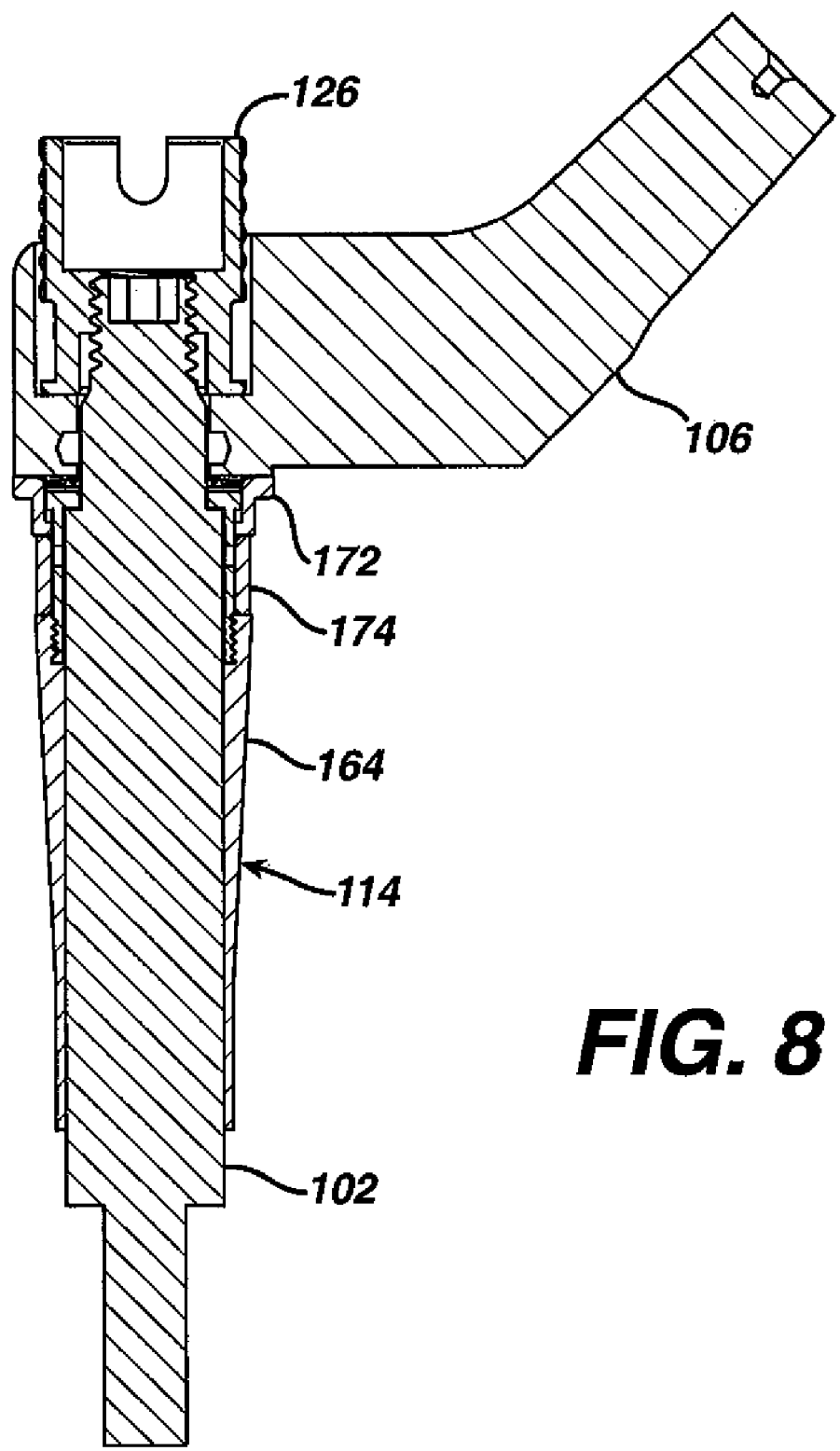
FIG. 8 is a/partial cross-sectional view of the modular trial of FIG. 1.
Figure 9:
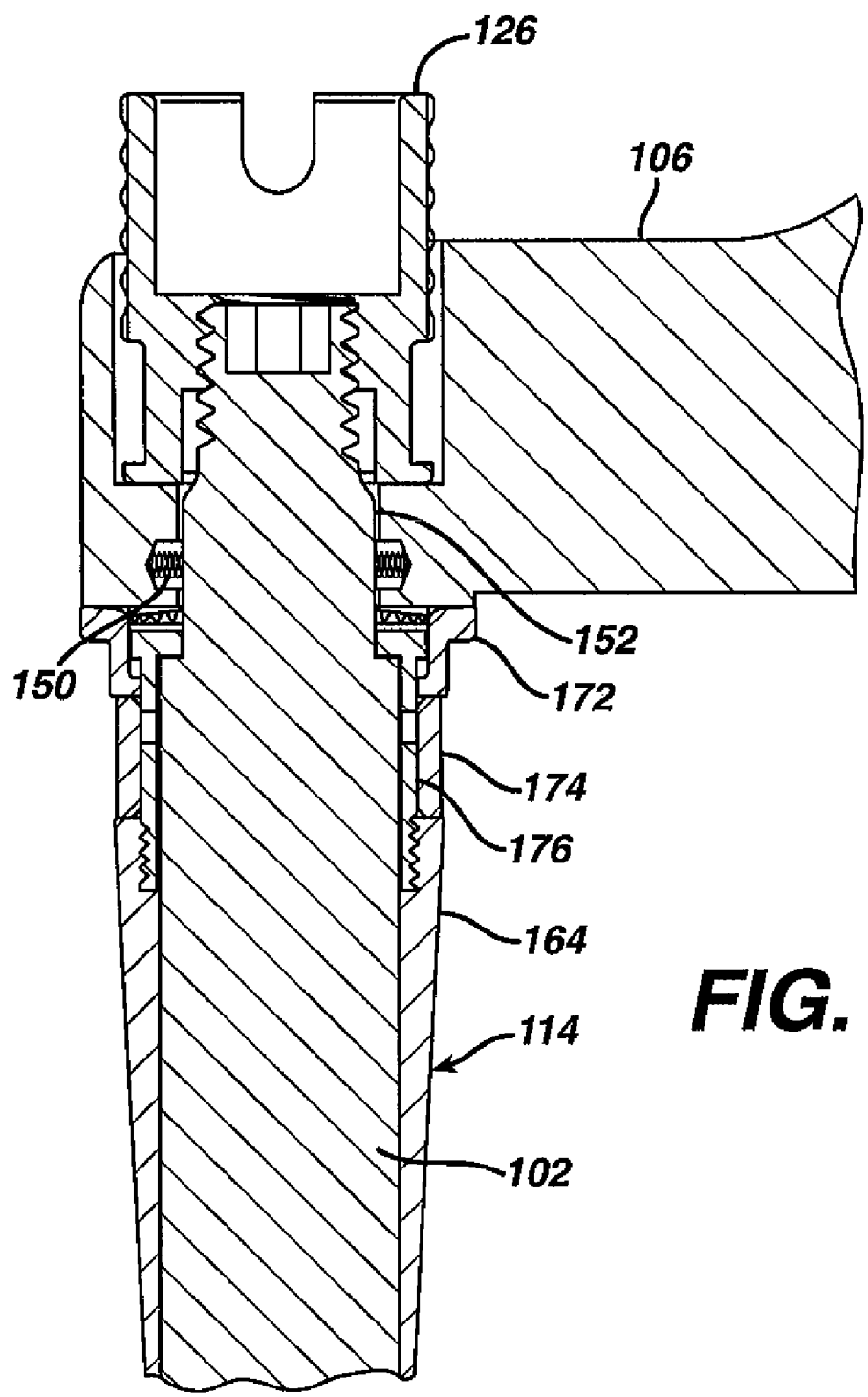
FIG. 9 is a partial cross-sectional view of the modular trial of FIG. 1.

When the proximal body trial assembly 114 including the sleeve 164, the ring 174, the spline 172 and the keyed component 156 are sandwiched between the stem 102 and the neck trial 106, the connector 126 is then threadably engaged into the external threads 162 of the stem 102. Until the connector nut 126 is fully torqued onto the stem 102, the ring 174 is free to rotate about centerline 104. Until the connector nut 126 is securely torqued against the stem 102, the neck trial 106 may be freely rotated with only the resistance of the spring 150 in the direction of arrows 178 to permit the adjustment for anteversion for the trial 100. To assist in permitting and torquing of the connector nut 126, the connector nut 126 may optionally have external splines or knurls 180. Referring to FIG. 6, the connector nut 126 may be permanently secured to the proximal body 106 by means of a pin 182 in the neck trial 106. When the pin 182 traps the connector nut 126 within the neck trial recess 184, the pin 182 limits motion of the connector nut 126 to within that of the connector nut groove 186.

Optionally, as shown in FIG. 5, the trial 100 may include an outer trial sleeve 130 that is used to replicate a prosthetic sleeve once the proximal body trial is loaded onto the distal stem. This sleeve 130 may be secured to this distal stem assembly by inner sleeve 164 which forms a slip fit with the tapered bore 136 of the outer sleeve 130.

Figure 10:
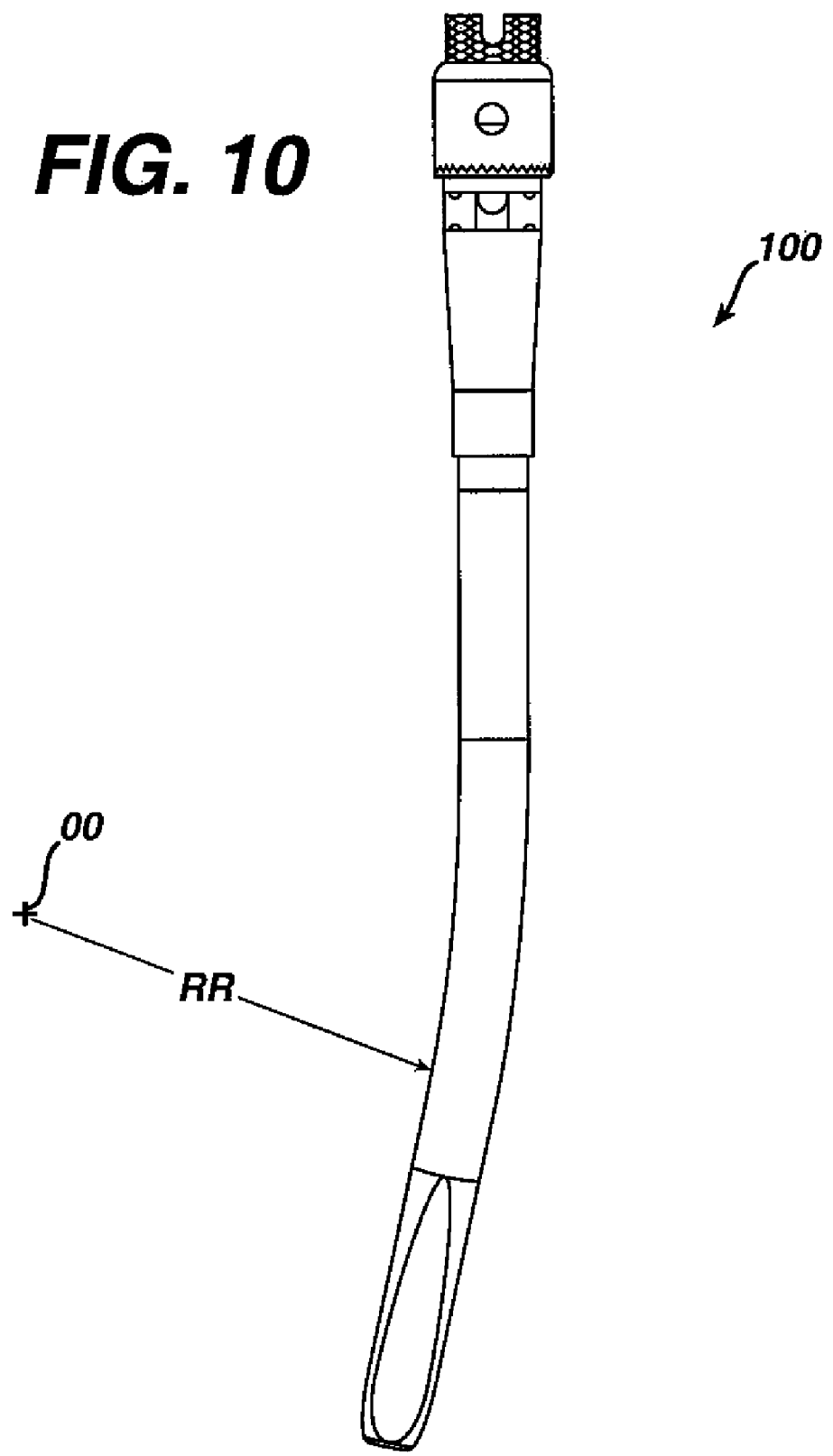
FIG. 10 is a side view of the modular trial of FIG. 9.

Referring now to FIG. 10, the curved distal stem portion 110 is shown with the curved distal stem 110 showing the full extent of the curve. The curved distal stem portion 110 may be defined, by example, a radius RR extending from an origin 00. The radius RR may be, for example, 4 to 8 inches, and may vary depending on the curvature of the patient's femoral intramedullary canal.

Figure 2:
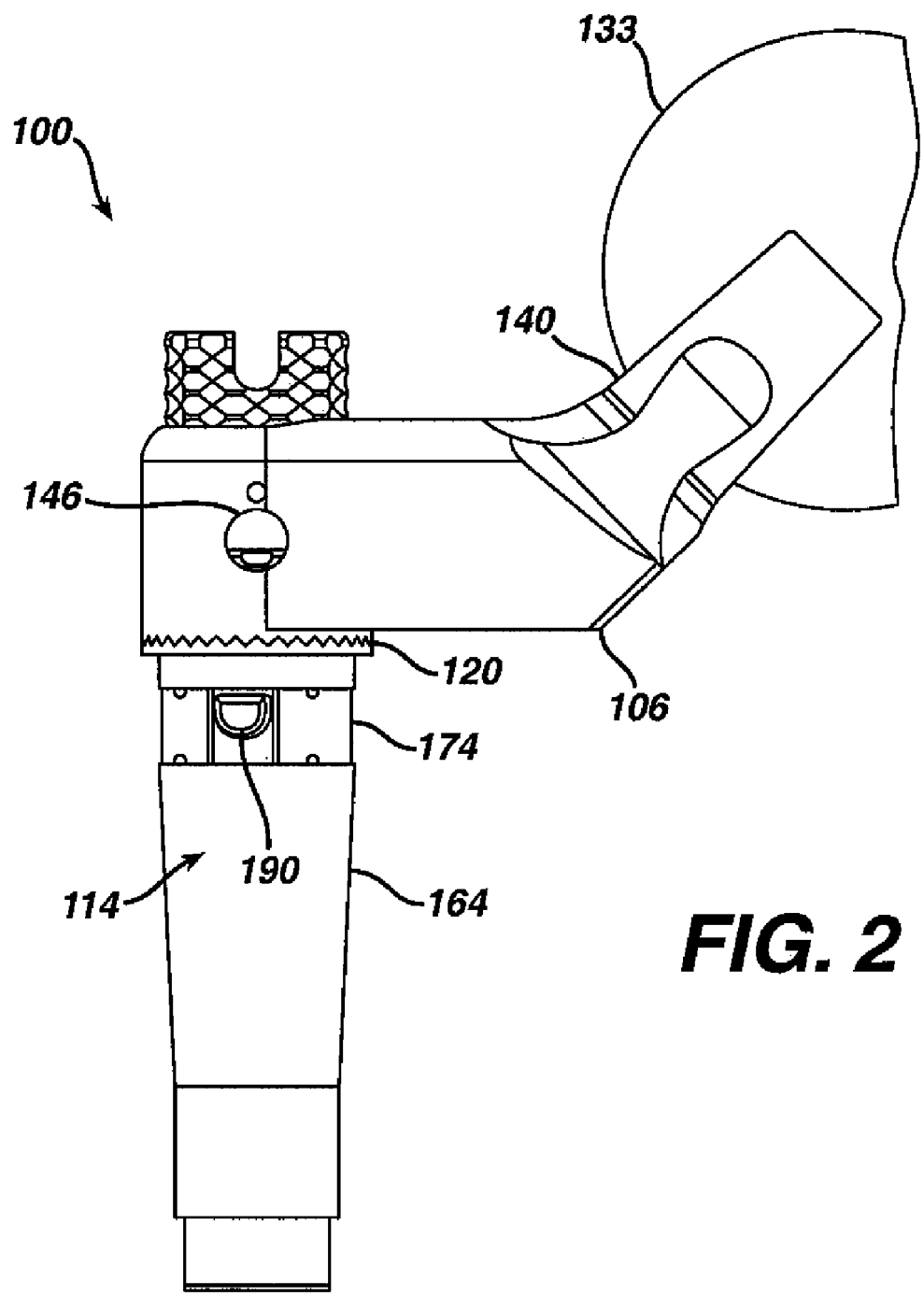
FIG. 2 is a partial plan view of the modular trial of FIG. 1.
Figure 3:
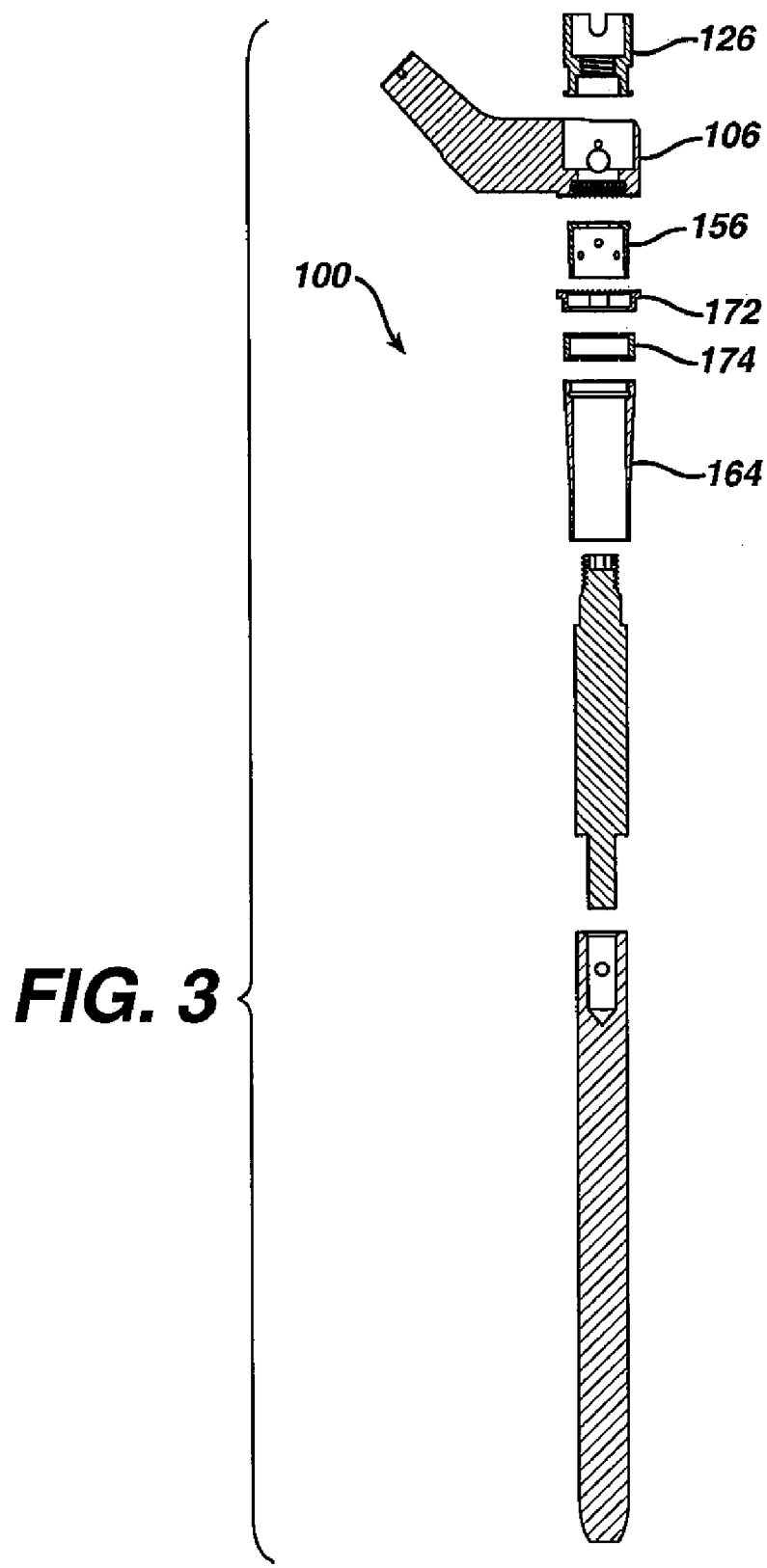
FIG. 3 is an exploded cross-sectional view of the modular trial of FIG. 1.

Referring now to FIG. 2, the neck trial portion 106 of the trial 100 may include a neck 140 to which a ball or head 133 may be used to fit against an acetabular cup (not shown) on the acetabulum of the patient.

Figure 11:
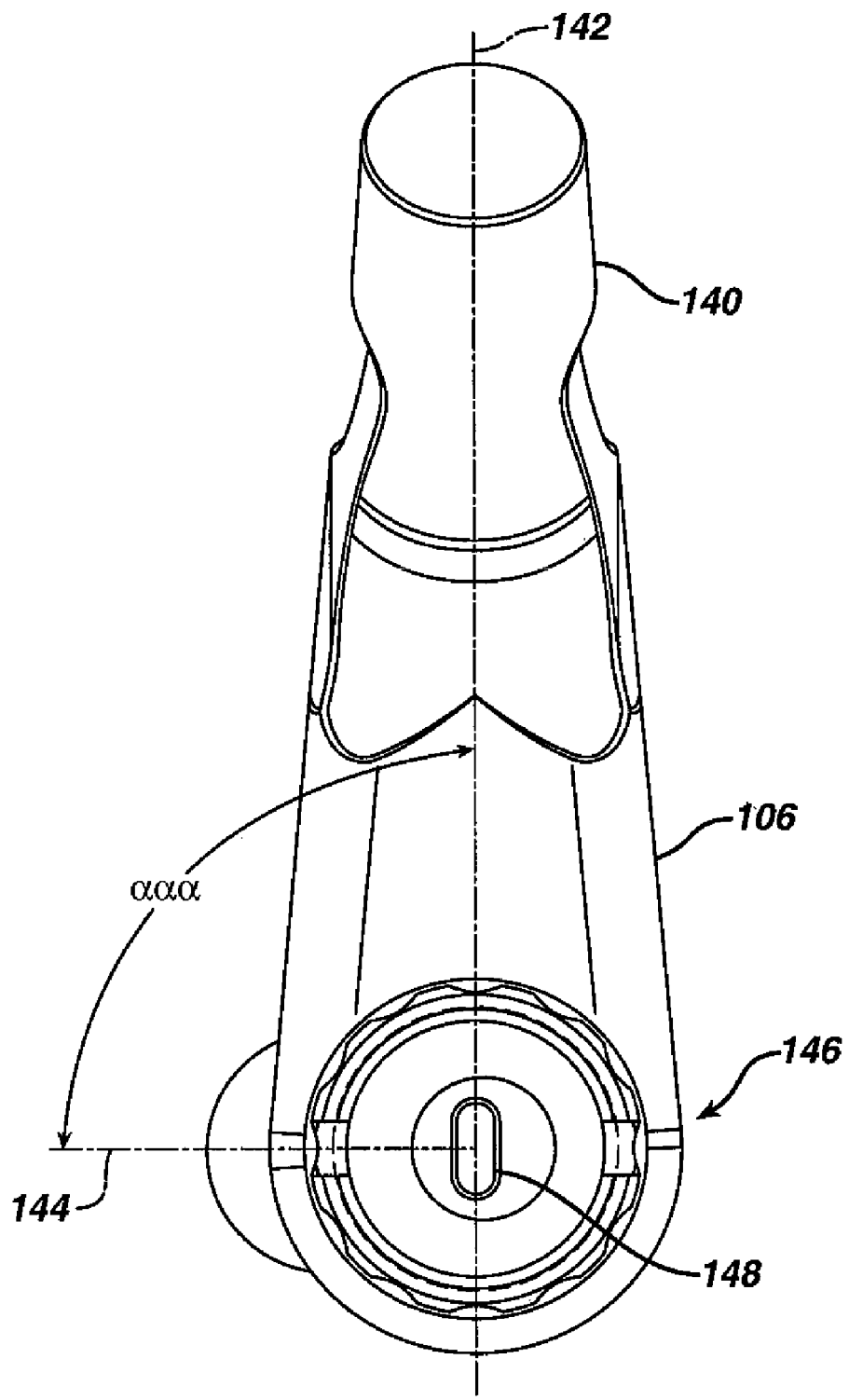
FIG. 11 is a top view of the modular trial of FIG. 1.
Figure 12:
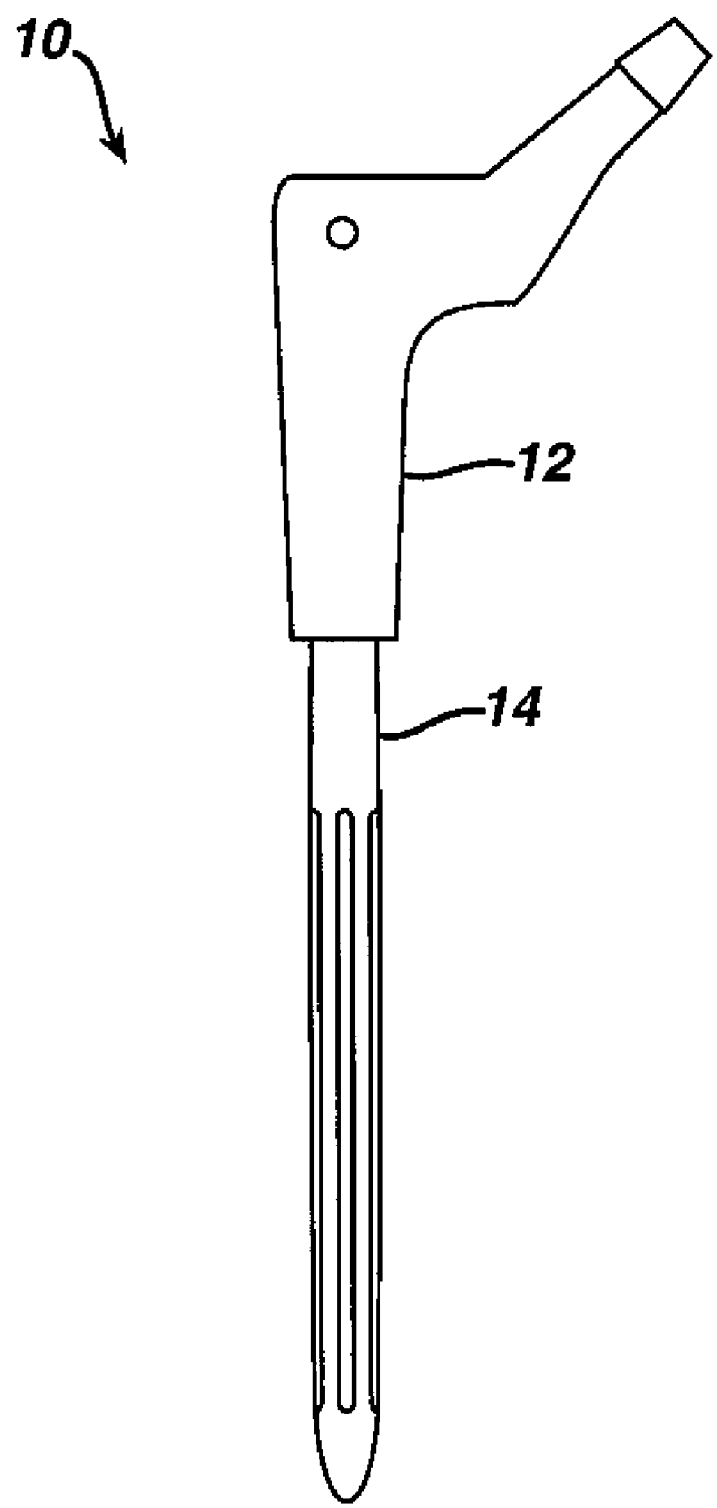
FIG. 12 is a plan view of a first embodiment of a modular hip stem for use in the medullary canal of a femur which may be used with the trial of the present invention to practice the surgical method of the present invention.

Referring now to FIGS. 1 and 11, the trial 100 preferably includes locating features to determine the relative angular position ααα between the neck centerline 142 and the stem centerline 144. For example, the neck trial 106 may include a body locating feature 146 while the distal stem assembly 102 may include a stem locating feature 148. The neck trial's locating feature 146 may be in the form of, for example, opposed cylindrical holes. The stem locating feature 148 may be, for example, in the form of a key way or oval-shaped slot in the proximal end of the distal stem assembly 102.

Preferably, so that the trial may be used with a variety of hip stems, the holes 146 should be used as a standard for those prostheses to which the trial is associated. Similarly, the slot 148 of the trial 100 should preferably be replicated in any prosthesis to which the trial of the present invention is to be used as a system. Preferably, in order that the position of the outer sleeve 130 may be replicated or measured during the trialing of a hip stem prosthesis utilizing the trial 100, the trial 100 includes pins 190 located in opposed directions on ring 174. The pins 190 are radially fitted to opposed slots 192 located on the outer sleeve 130. As the outer sleeve 130 is positioned in the proper location to properly anchor the trial 100, the angular position of the outer sleeve 130 can be locked and its position recorded by the tightening of the connector nut 126. When the connector nut 126 is secured against the stem 102, the spline member 172 and sleeve 164 place an axial load against the faces 194 of the ring 174, locking it into a fixed angular position, thus locking the construct comprised of the neck trial 106, stem trial 102 and outer sleeve trial 130. The outer sleeve 130 is thereby locked into an angular position that may be duplicated later on an implant.

Referring now to FIGS. 12 through 19, an alternative modular hip implant embodiment is shown which may be used in conjunction with the trial 100 of the present invention to accomplish a method of trialing according to the present invention. The hip stem 10 is suitable for use with the illustrated trial 100 or with other embodiments of such a trial. The hip stem 10 may be made of any suitable durable material that is compatible with the human body. For example, the hip stem 10 may be made of a titanium alloy, a cobalt chromium alloy, or a stainless steel. As shown in FIGS. 12 through 19, the hip stem 10 includes a proximal body 12 and bowed distal stem 14.

Figure 18:
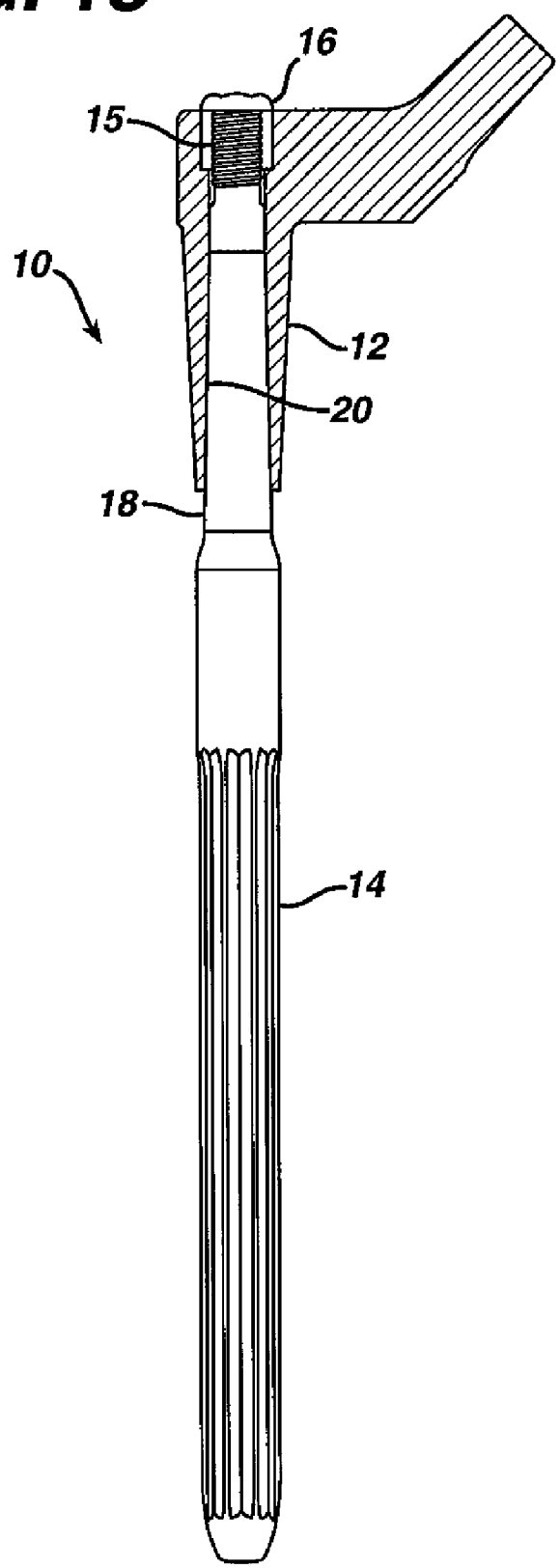
FIG. 18 is a plan view partially in cross-section of the modular hip stem of FIG. 20 showing the distal stem portion in greater detail.

Referring now to FIG. 18, the proximal body implant 12 may be secured to the distal stem 14 in any suitable fashion. For example, and as shown in FIG. 18, the proximal body 12 may be secured to the distal stem 14 by means of threads 15 located on the proximal portion of the proximal body 12, which are threadably engaged to a nut 16. In addition and as shown in FIG. 18, the distal stem 14 may include an external tapered portion 18 which mates with an internal tapered portion 20 of the proximal body 12. The taper of the internal tapered portion 20 and the external tapered portion 18 may be defined by an angle φ. Preferably, the taper is self-locking and has an angle φ of, for example, approximately 18 degrees or less.

Figure 13:
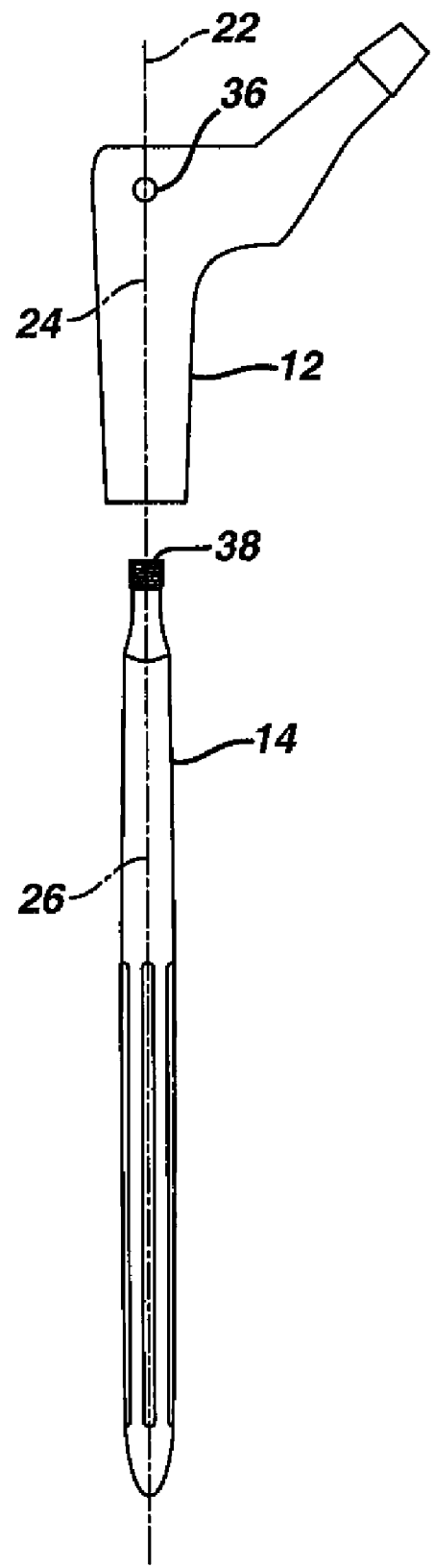
FIG. 13 is an exploded view of the hip stem of FIG. 12.

Referring now to FIG. 13, the proximal body 12 and the distal stem 14 may either or both be rotatable around longitudinal centerline 22. For example, the proximal body 22 may be rotatable in the direction of arrows 24 and the distal body may be rotated in the direction of arrows 26.

Referring now to FIGS. 16 and 16A, a patient's femur is shown at 27. The natural femur 27 has an anatomical anteversion. As shown in FIG. 16, the normal femur is bowed anteriorly. In the present invention, the anatomical anteversion angle α is defined by a plane, shown at 29 in FIGS. 16 and 16A, through the anterior bow 31 of the femur, and a line through the center of the femoral neck, shown at 33 in FIGS. 16 and 16A. The plane 29 corresponds with the position of the intramedullary canal. Since the stem of the prosthesis will be received in the intramedullary canal, in the present invention, the anatomical anteversion of the femur can provide the basis for setting the prosthesis anteversion. In the following description and in the drawings, the reference a is used for the anatomical anteversion angle as defined above; the reference αα is used for the prosthetic or assembly anteversion angle. The prosthetic or assembly anteversion angle is defined by a plane through the bowed stem of the prosthesis and a line through the neck of the proximal part of the prosthesis. In at least one aspect of the present invention, a trial anteversion angle ααα between a plane through the stem and the neck of the trial can be based on data gathered preoperatively and can be adjusted by the surgeon intraoperatively to adjust the trial; the surgeon can use this data to assemble the modular prosthetic implant. Such a trial anteversion angle is illustrated in FIG. 11. Thus, through use of the present invention, the surgeon should be able to assemble a prosthesis such that the prosthetic or assembly anteversion angle αα approximates the anatomical anteversion angle α. However, it should be understood that other landmarks could be used to determine the anatomic anteversion angle, and unless expressly called for in the claims, the present invention is not limited to any particular reference for the anatomic anteversion angle. For example, the anatomic anteversion angle could be determined from the position of the patient's foot with respect to the patient's shoulder line. It should also be understood that the principles of the present invention could also be applied to other prosthetic joints, such as shoulders, and the reference for the anatomic anteversion angle will depend on anatomic features of the bones comprising that joint. In addition, because of factors such as placement of the acetabular component of the prosthetic implant, the surgeon may determine that the optimum prosthetic anteversion angle αα should vary somewhat from the anatomic anteversion angle α. With the present invention, the surgeon can make such adjustments intraoperatively.

Referring now to FIG. 17, the angular position between the neck 32 of the proximal body and the distal curved portion 34 of the curved distal stem 14 form the prosthetic anteversion angle αα. The anteversion angle αα affects the patient's ability to function and the patient's gait.

As shown in FIG. 13, the hip stem 10 includes a proximal body location feature in the form of holes 36. It should be appreciated that the holes 36 should be designed of the same shape and location as the holes 146 of the trial 100. Similarly, the distal stem includes a distal stem location feature in the form of, for example, a slot 38. It should be appreciated that the slot 38 should be made compatible and have the same size and shape as the slot 148 of the trial 100. The proximal body location feature 36 and the distal stem location 38 may have any suitable shape and may be in the form of, for example, slots, indents, triangles, squares, polygons or any indexable feature.

Figure 14:
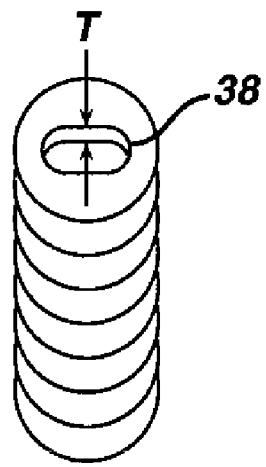
FIG. 14 is a partial perspective view of the modular hip stem of FIG. 12 showing the keying slot.
Figure 15:
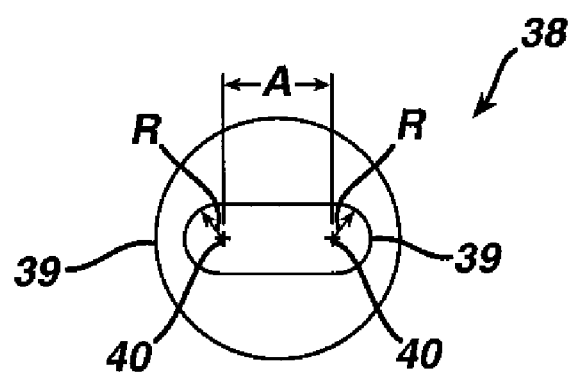
FIG. 15 is a partial top view of the stem of FIG. 12 showing the keying slot.
Figure 19:
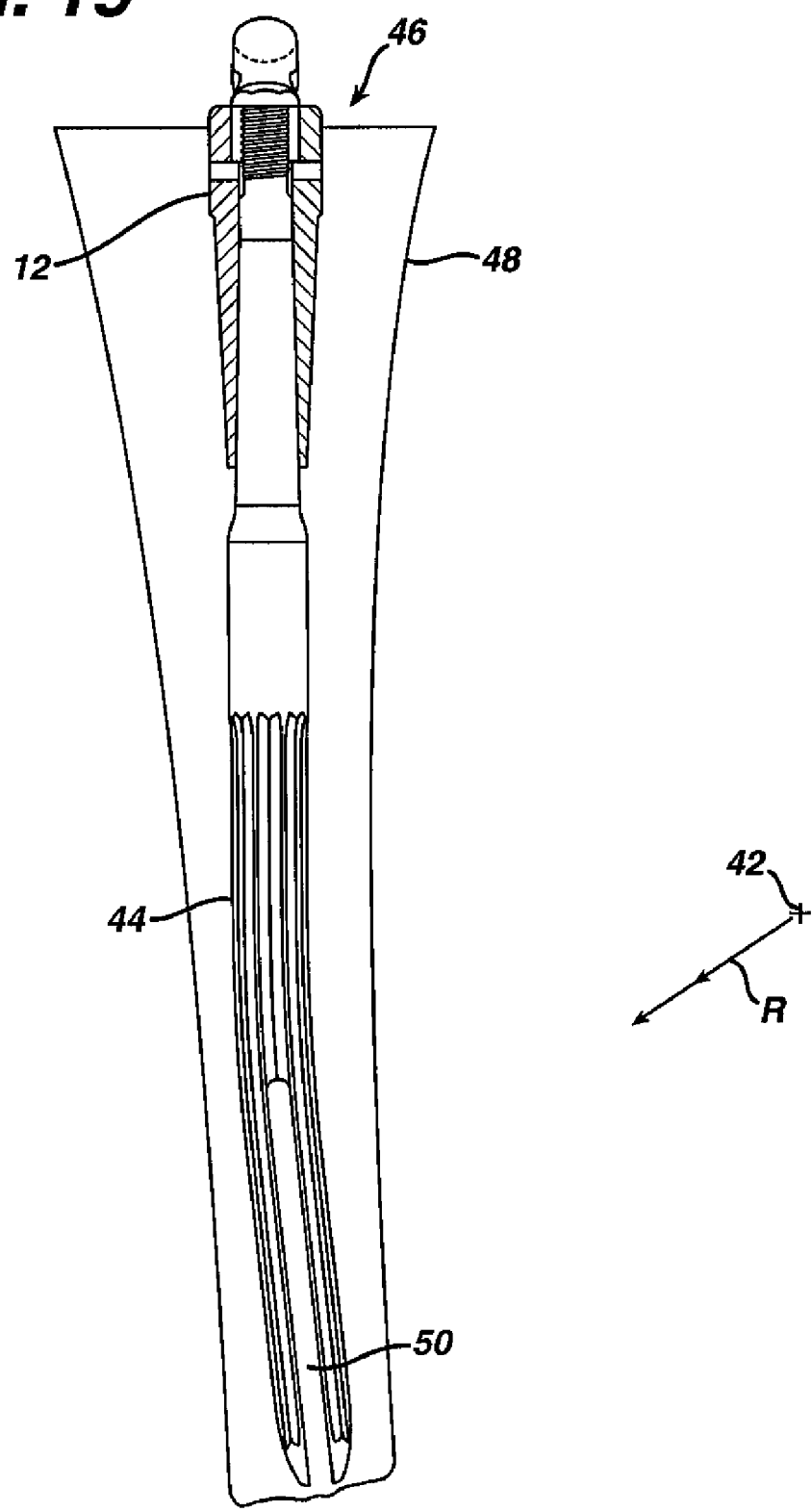
FIG. 19 is a side view partially in cross-section of the modular hip stem of FIG. 20.
Figure 20:
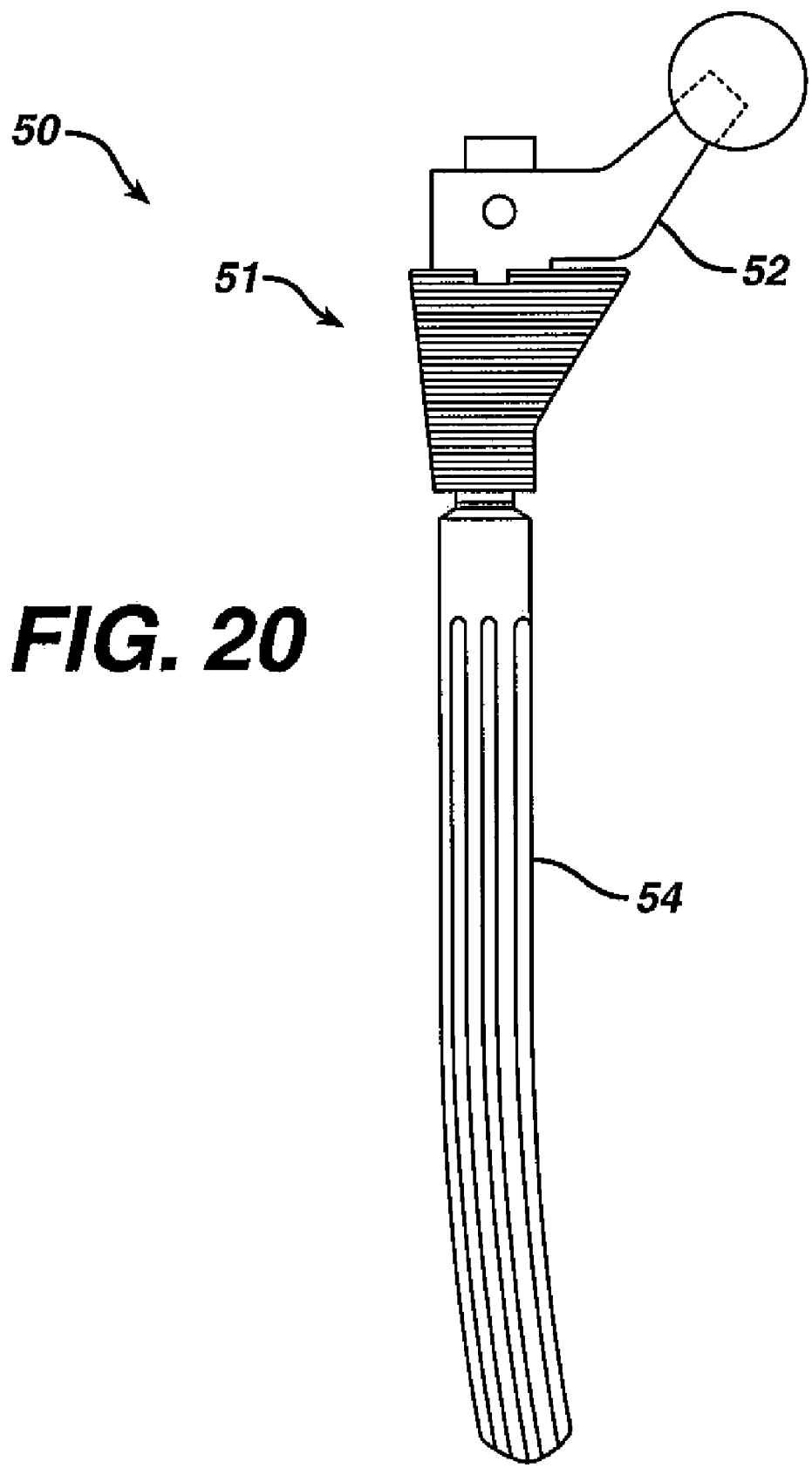
FIG. 20 is a plan view of another embodiment of a modular hip stem which may be used with the trial of the present invention to practice the surgical method of the present invention.
Figure 21:
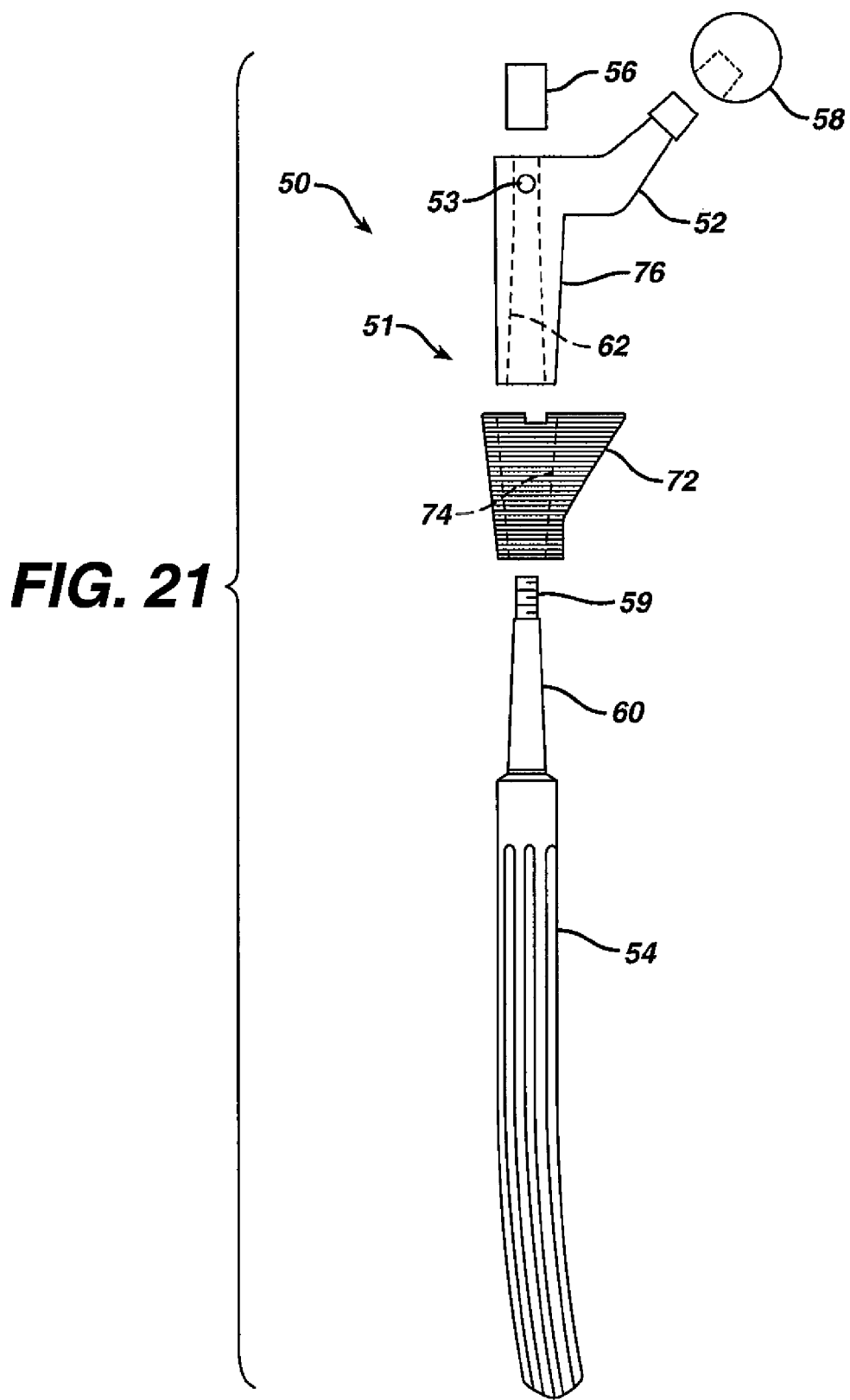
FIG. 21 is an exploded view of the hip stem of FIG. 20.

Referring to FIGS. 14 and 15, the slot 38 is shown in greater detail. As shown in FIG. 15, the slot 38 may include two arcuate portions 39 defined by radius R extending from center points 40. The center points 40 may be spaced from each other a distance, for example, A. The slot may have a depth T of, for example, 0.1 to 0.7 inches. Referring now to FIG. 19, the distal stem 14 is shown in location where the arcuate the shape of the distal stem is most pronounced. The curvature of the distal stem 14 may be defined by a radius R extending from a distal stem center point 42. The distal arcuate stem 14 is fitted into arcuate portion 44 of the medullary canal 46 of the femur 48. The distal stem 14 may further include a slot 50 to assist in the positioning of the arcuate femur 48 into the arcuate medullary canal 46 of the femur 48.

Referring now to FIGS. 20 through 23, another embodiment of the hip stem for use in a hip prosthesis that may utilize the trial and surgical procedure of the present invention is shown. Hip stem assembly 50 includes stem 54. The stem 54 includes a proximal body 52 and a distal stem 54. Like the stem 10 of FIG. 12, the proximal body 52 of the stem 54 may be secured to the distal stem 54 through an internal taper 62 in the proximal body 52, which is mateable with the external taper 60 on the distal stem 54. It should be appreciated that the tapers 60 and 62 are preferably self-locking as in the stem 10. A ball or head 58 that mates with a cup (not shown) secured to an acetabulum (not shown) may be located on the proximal body. The distal stem 54 and the proximal body 52 may further be secured to each other by means of, for example, a nut 56 that is threadably engaged to a threaded portion 59 of the distal stem 54. Similar to the stem 10 of FIGS. 12 through 19, the stem 54 includes a first location feature 66 associated with the distal stem 54 and a second alignment feature 53 associated with the proximal body 52.

Figure 22:
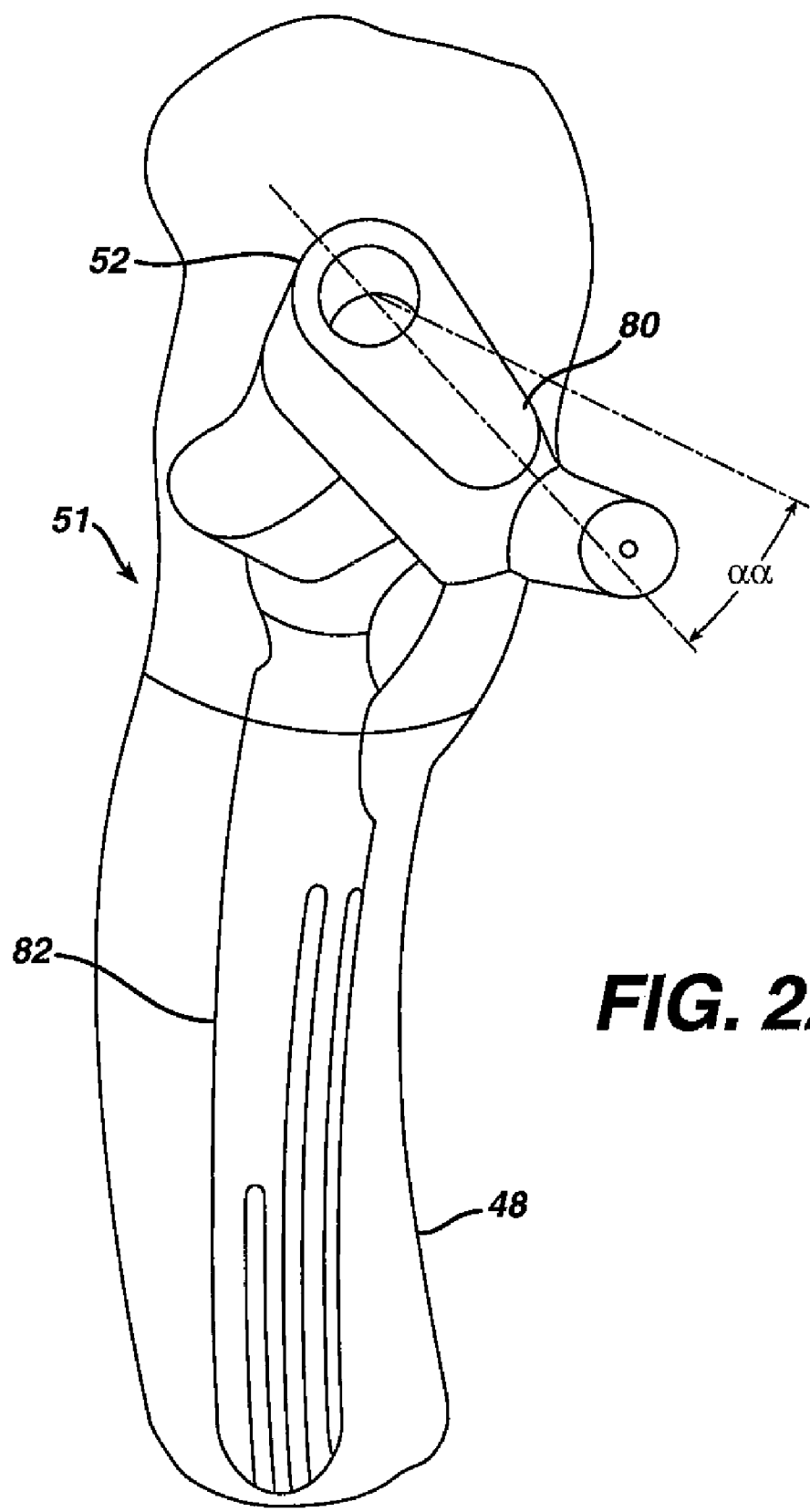
FIG. 22 is a perspective view of the modular hip stem of FIG. 20 showing the implant in a femur.

The first alignment feature may be in the form of a recess 66 with a feature that can transmit torque. For example, the first alignment feature 66 may be in the form of a triangular opening, a rectangular opening, a philips screw slot, a screw slot, or as shown in FIG. 22, in the form of a oval slot. The slot 66 of the stem 54 may be made to similar dimensions to that of slot 38 of the hip stem 10.

The hip stem 54 may include, in addition to the components already mentioned, a sleeve 72 that may mate with the proximal body 52. The sleeve 72 may include a bore with an internal taper 74 which mates with the external taper 76 on the proximal body 52. The sleeve 72 serves to provides additional support for the prosthesis 51 in the metaphyseal region and provides increased stability for the prosthetic stem 54 when the stem receives torsional loads.

The second alignment feature 53 may be in the form of a pair of post holes that are similar to the holes 36 of the hip prosthesis 10.

Figure 23:
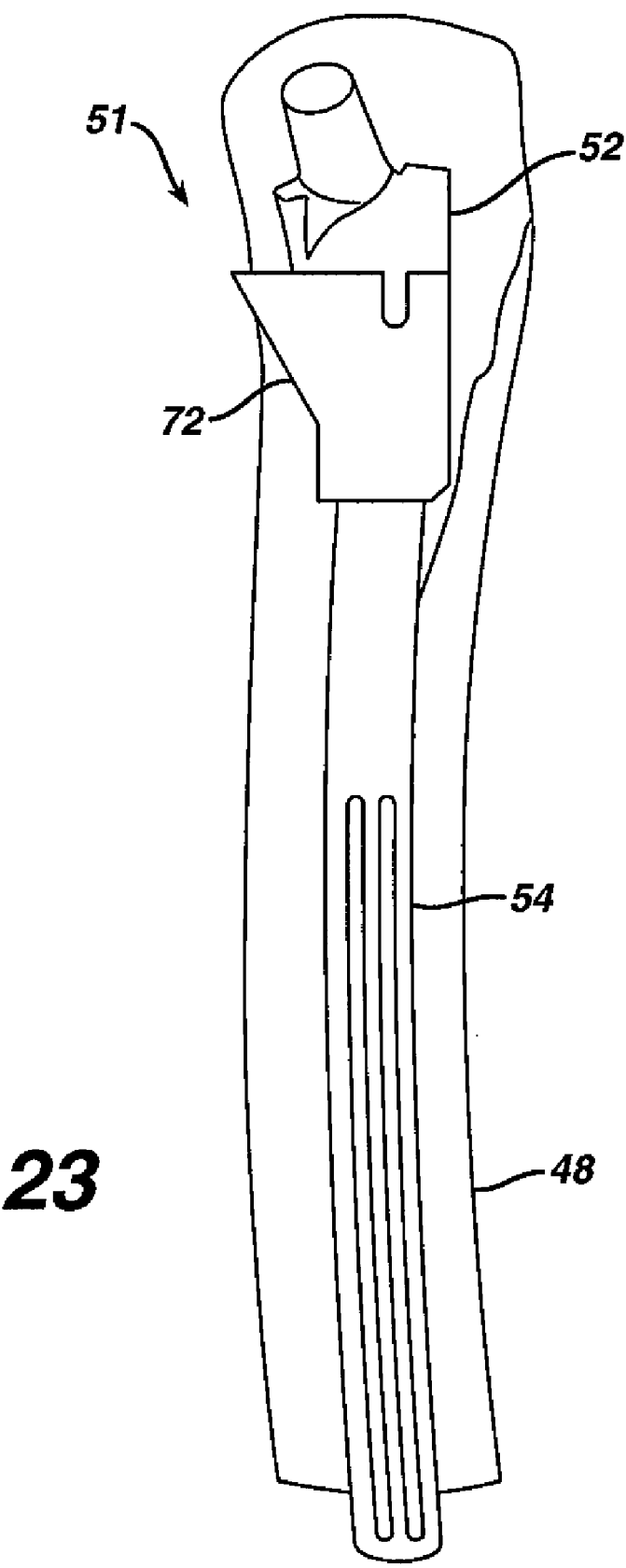
FIG. 23 is another perspective view of the modular hip stem of FIG. 20 showing the stem in a femur.

Referring now FIGS. 22 and 23, the hip stem assembly or construct 51 is shown in position in the long bone or femur 48. The proximal body 52 is shown in position with the neck 80 and the bowed portion 82 of the distal stem 54 being out of angular alignment. The angle between the neck 80 and the arcuate portion 82 is defined by prosthetic anteversion angle αα. It should be appreciated that in FIGS. 20 and 21, the distal stem 54 is out of angular position with respect to neck.

Figure 24:
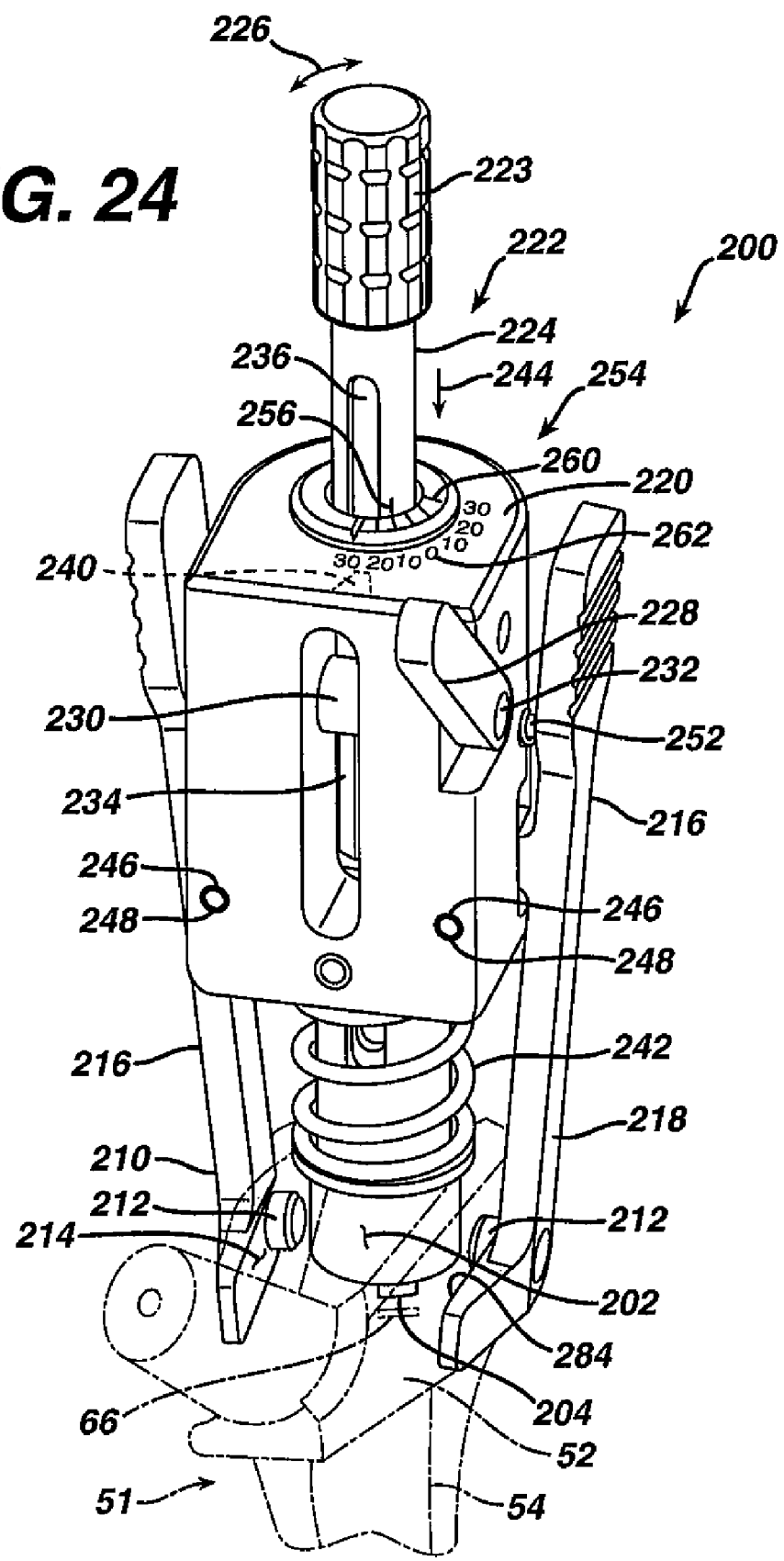
FIG. 24 is a perspective view of an alignment tool that may be used to register the alignment of the modular trial of FIG. 1 or the hip stems of FIGS. 12 and 20 shown in position on the modular trial for registering the alignment the modular trial of FIG. 1.
Figure 25:
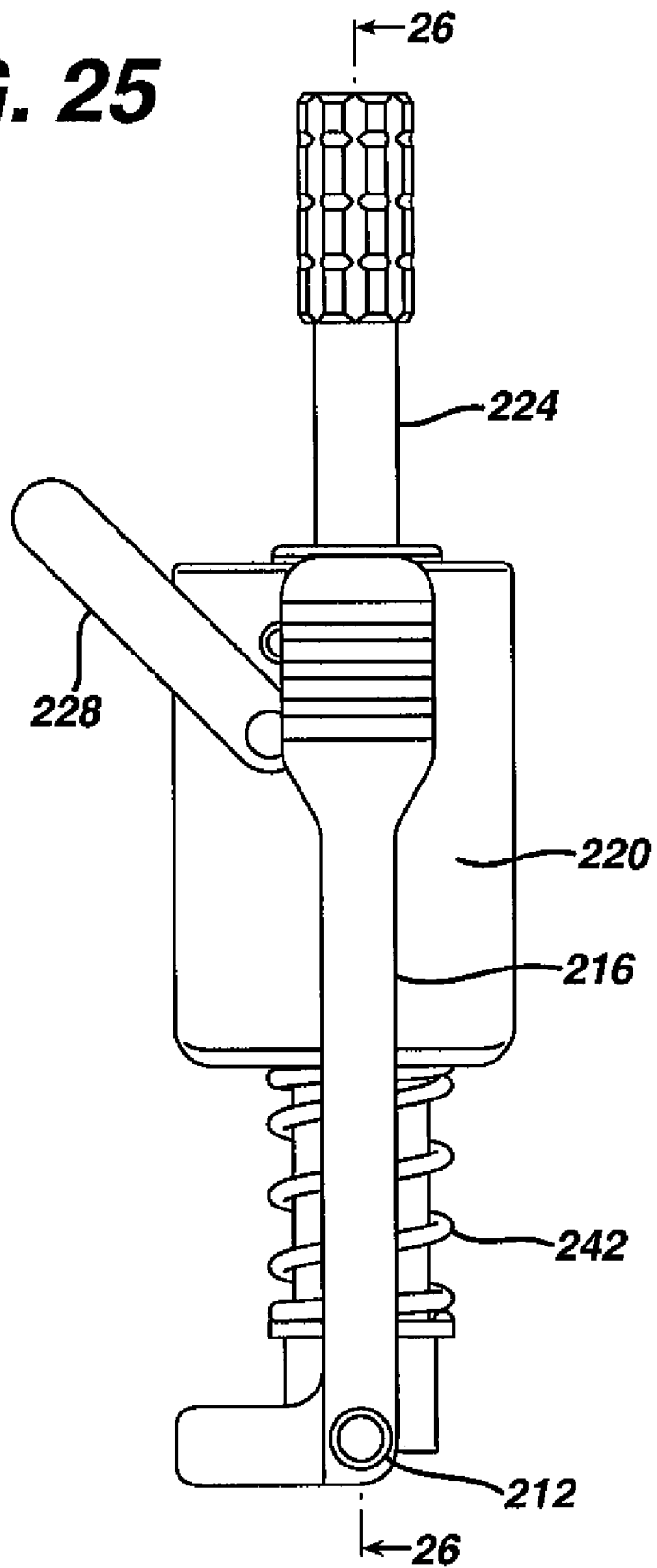
FIG. 25 is a side view of the alignment tool of FIG. 24.
Figure 26:
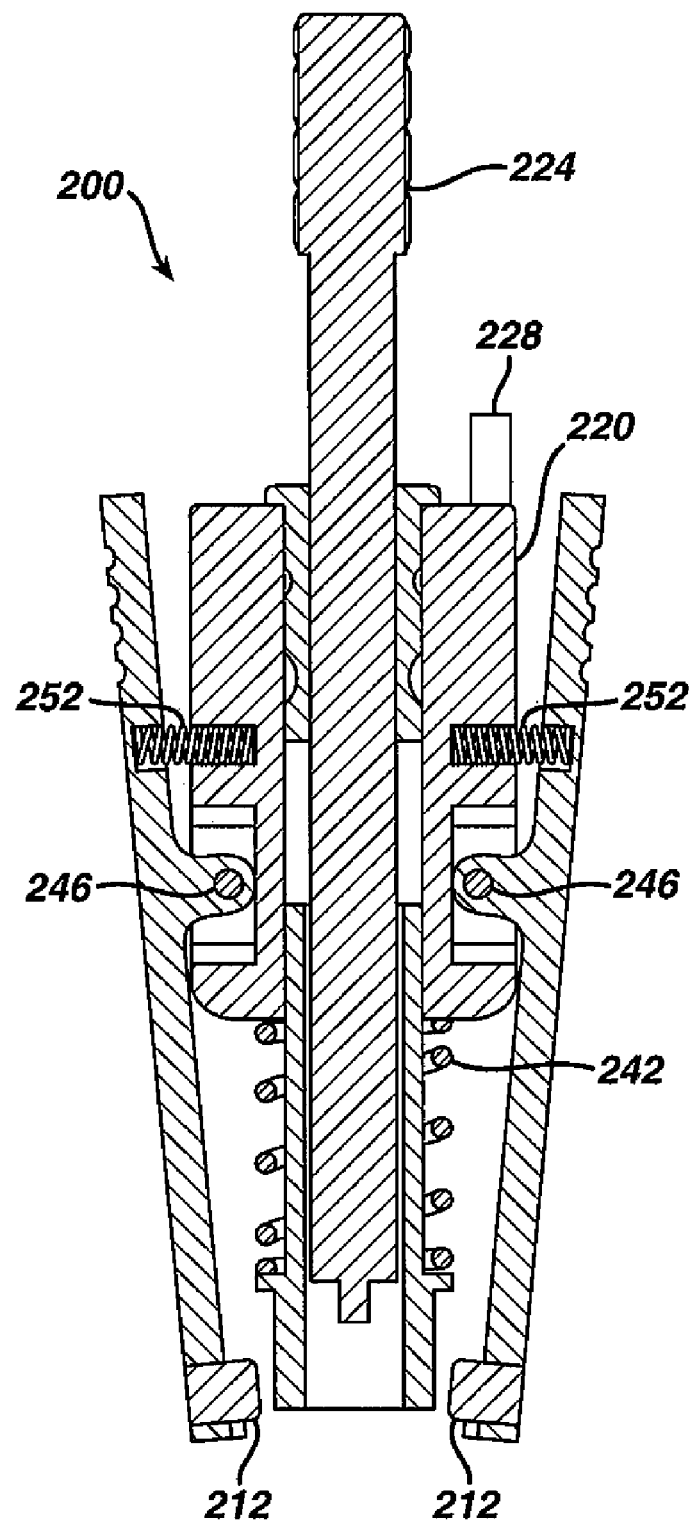
FIG. 26 is a cross-sectional view of FIG. 25 along the line 26-26 in the direction of the arrows.
Figure 27:
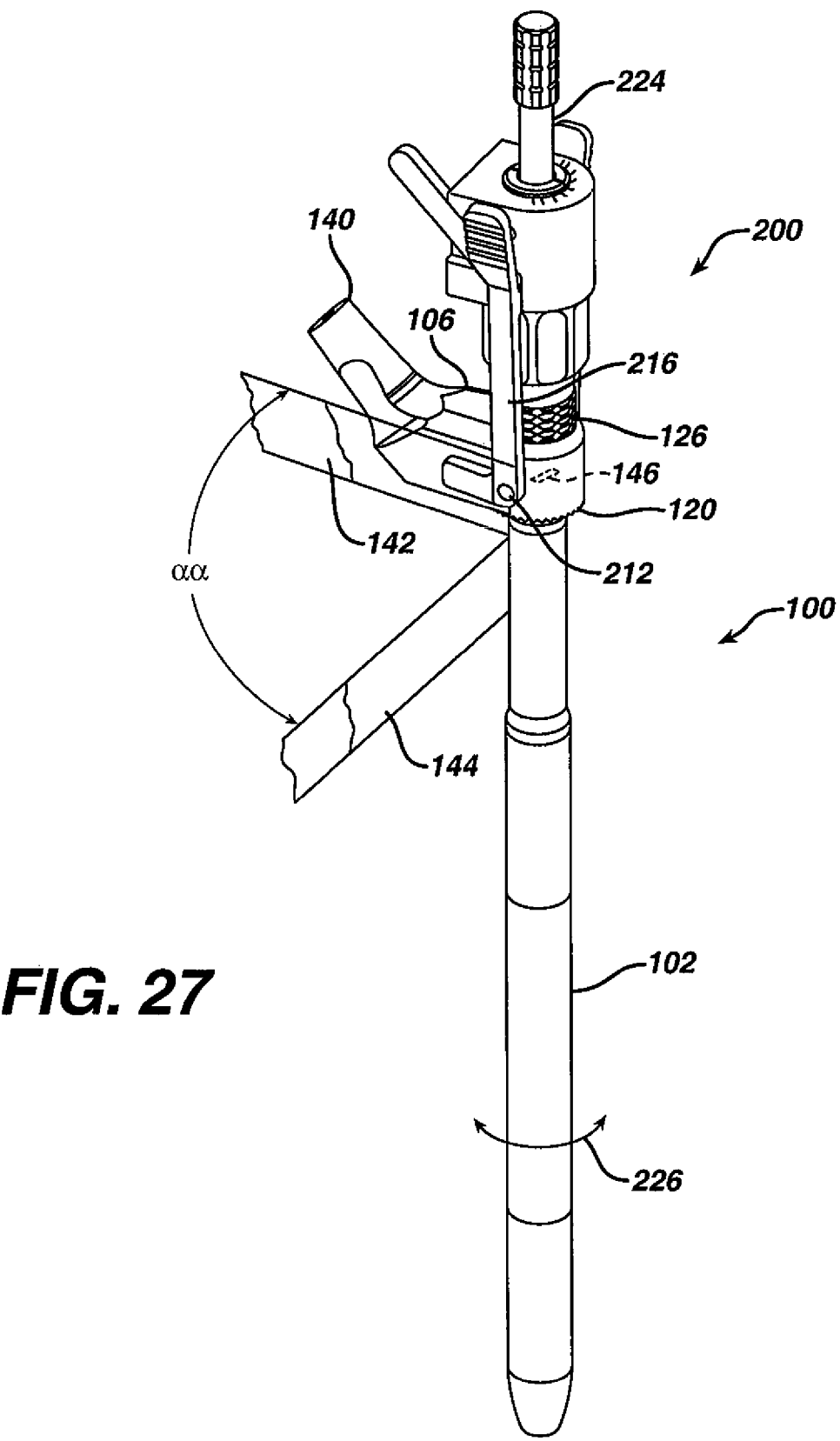
FIG. 27 is a perspective view of the alignment tool of FIG. 24 in position on the trial of FIG. 1.
Figure 28:
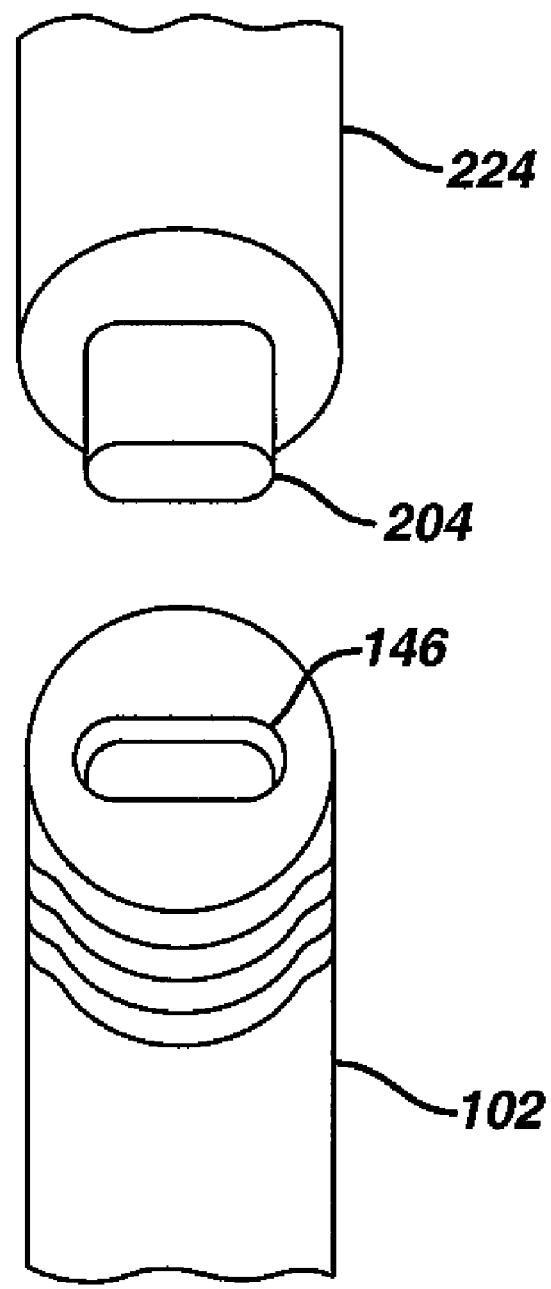
FIG. 28 is a partial perspective view of FIG. 25 showing the keyed timing of the distal stem of the trial and/or distal stem implant with the alignment tool.

Referring now to FIG. 24, an instrument 200 is shown for use with the trial 100 of the present invention as well as with the stem 10 and the hip stem 51 to perform the surgical procedure of the present invention. The instrument 200 may be utilized with either implants or trials. For example, the instrument 200 may be utilized with the trial 100 of FIGS. 1 through 11, or with the hip stem 10 of FIGS. 12 through 19. Likewise, the instrument 200 may be used with the hip stem 51 of FIGS. 20 through 23.

The instrument 200 is used in conjunction with the relative angular orientation of a first component of a multi-piece prosthesis to a second component of a multiple piece prosthesis. The instrument 200 may be utilized to observe the relative angular orientation of the components and to replicate the angular orientation of the first component relative to the second component. While the instrument 200 may be adapted for any of a large number of designs of prosthetic components and prosthetic trial components, including the hip stem 10, the hip stem 51 and the trial 100, the instrument 200 will for simplicity now be described for use with the hip stem 51 of FIGS. 20 through 23.

Continuing to refer to FIG. 1, the instrument 200 is utilized for at least one of observing or replicating the relative angular orientation of a first component, for example, proximal body 52 of the prosthesis with respect to a second component, for example, hip stem 54 of the prosthesis for use in joint arthroplasty.

The instrument 200 includes a first member 202 for cooperation with the first component 52. The second member 202 may have any suitable size and shape capable for cooperation with the first component 52. As shown in FIG. 24, the first member 202 may include a first member keyed feature 204. The first member keyed feature 204 cooperates with a first component keyed feature, for example, slot 66 of the first component 54. The keyed features 204 and 66 are used to angularly link the first member 202 with the first component 54.

The keyed features 204 and 66 may have any suitable size and shape such that the first member 202 and the first component 54 are in timed engagement to provide a rotational linkage of the first member 202 to the second component 54 about longitudinal centerline 206 of the instrument 200. The first keyed feature 204 may be in the form, for example, of a recess or, as shown in FIG. 1, in the form of a protrusion. For cooperating with, for example, the slot of the hip stem 50, the keyed feature 204 may be in the form of an oval protrusion. It should be appreciated that the keyed feature 204 may be a recess or a protrusion or may be square, triangular, rectangular, a polygon, or any shape capable of transmitting torque.

The instrument 200 further includes a second member 210 for cooperation with the first component 52. The second member 210 may be in cooperation with the second component 52 in any suitable manner. For example, the second member 210 may include a second member keyed feature 212, which cooperates with, for example, the second component keyed feature in the form of holes 53. The second member keyed feature 212 may have any suitable form and may, for example, be in the form of a pin 212, a flap 214, an arm 216, or in the form of a yoke (not shown).

For the instrument 200 to cooperate with the holes 53 in the hip prosthesis 50, the instrument 200 includes the pin 212 extending inwardly from the arm 216. To enhance the stability of the instrument 200, the instrument 200 may further include a stabilizing member 218 similar to the second member 210, but being a mirror image of the second member to attach to the opposite side of the second component. The stabilizing member 218 also includes the arm 216, pin 212 and the flap 214.

Continuing to refer to FIG. 24, the instrument 200 further includes a feature 220 for cooperation with the first member 202 and the second member 210 for at least one of replicating or observing the relative angular orientation of the first component with respect to the second component 52. The feature 220 may be in the form, for example, a body. At least one of the first member 202 and the second member 210 are movably connected to the body 220. The body 220 serves the purpose of operably interconnecting the first member 202 to the second member 210. With the use of the body 200, the first member 202 may be positioned appropriate relative to the second member 210 to replicate or observe the relative angular orientation of the first component 54 with respect to the second component 52.

For example, and as shown in FIG. 24, the body 220 may include a longitudinal opening 222 into which an orientation rod 224 is slidably movable along longitudinal axis 206. The first member keyed feature 204 may be located on an end of the orientation rod 224. The orientation rod 224 may include a gripping feature 223 in the form of, for example, flaps or splines for assisting in attempting to move the orientation rod 224 axlely along the longitudinal centerline 206 and to rotate the orientation rod 224 in the direction of arrows 226.

As shown in FIG. 24, the orientation rod 224 and the keyed feature 204 may be angularly oriented with respect to the body 220 electively permitting and preventing the orientation rod 224 from rotating in the direction of arrows 226. Such selective rotation of the orientation rod 224 may be accomplished by any method.

For example, the body 220 may include a locking arm 228 connected to a cam 230 by shaft 232 mounted to the body 220. The cam 230 may utilized to selectively lock the orientation rod 224 in a fixed position with respect to the body 220 or, as shown in FIG. 24, may merely prevent the orientation rod from rotating in the direction of arrows 226.

In order that the locking arms 228 may be utilized to prohibit rotation in the direction of arrow 226 while permitting the movement of the orientation rod 224 along the axis of the longitudinal centerline 226, the body 220 may further include a bushing or sleeve 234. The sleeve 234 is rotatably fitted to the opening 222 in the body 220. The cam 230 selectively engages the sleeve 234 to prevent and permit relative motion of the sleeve 234 with respect to the body 220. The sleeve 234 may be operatively connected to the orientation rod 224 such that the orientation rod 224 may move along the longitudinal axis 206 but prohibit it from relative motion with respect to the sleeve 234 rotationally in the direction of arrow 226.

One method, as shown in FIG. 1, of preventing rotation of the orientation rod 224 with respect to the sleeve 234 is by providing, for example, a longitudinal groove in the orientation rod 224 that cooperates with a protrusion 240 extending inwardly from the sleeve 234. To keep the keyed feature 204 of the orientation rod 224 in full engagement with the slot 66 of the hip prosthesis 50, the instrument 200 may include a spring 242 positioned between the orientation rod 224 and the body 220 towards the orientation rod 224 and the keyed feature 204 downwardly in the direction of arrow 244.

As shown in FIG. 24, the second member 210 is rotatably fixedly secured to the body 220 about the longitudinal axis 206. To assure that the pin 212 is fully engaged in hole 53 of the prosthesis 50, the arm 216 may, as shown in FIG. 24, pivot about pin 246 secured at hole 248 of the body 220. Similarly, the stabilizing member 218 engages the other hole 53 of first component 54 at pin 212 and is pivotably positioned with respect to the body 220 at pin 246 secured to hole 248 in the body 220. The second member 210 and the stabilizing member 218 are preferably urged in the direction of arrows 250 toward the second component 52 by means of springs 252 positioned between the arms 216 and the body 220.

To measure the relative position of the first member 202 with respect to the second member 220 and correspondingly, the relative angular position of the first component 54 to the second component 52, the instrument 200 may include indicia 254 located on the instrument 200 providing measuring scale for the relative position of the first member 202 with respect to the second member 210.

The indicia 254 may have any suitable size and shape capable of providing the measurement capability for the instrument 200. The indicia 254 may, for example, include a single indicia in the form of a mark 256 extending axlely along orientation rod 224. The indicia 254 may further include a plurality of indicia in the form of body indicia 260 located on the sleeve 234 of the body 220. Numbers 262 may be located adjacent their respective body indicia 260. The numbers 262 may correlate to, for example, a particular degree of anteversion.

Referring now to FIGS. 27 through 30, the trial 100 of the present invention is shown with the instrument 200 in position on the trial 100. The instrument 200 is secured in position on the trial 100. The pins 212 on the arm 216 are engaged in the holes 146 of the proximal body 106 of the trial 100. Similarly, the key 204 of the orientation rod 224 of the instrument 200 is engaged in slot 146 of the stem assembly 102 of the trial 100. By loosening the nut 126 from the stem assembly 102, the proximal body 106 may rotate in the direction of arrows 226 with respect to the distal stem assembly 102. Stem center plane 144 and the neck center plane 142 define an included β of the trial 100.

By radiograph, CT scan or other imaging techniques, a patient's anatomic anteversion angle α may be determined. In typical cases, this anatomic anteversion angle α will be the optimum prosthetic anteversion αα. The trial 100 may be set by the instrument 200 so that the trial anteversion angle ααα equals the optimum anteversion angle of, for example, 90 degrees. Once the optimum trial anteversion angle ααα has been determined and set, the nut 126 may be tightened onto the distal stem assembly causing the index mechanism 120 to securely lock. Once securely locked, the index mechanism may prevent the rotation of the neck 140 with respect to the distal stem assembly 102.

It should be appreciated that the indicia 254 on the instrument 200 may be utilized either to save predetermined anteversion angle determined by radiograph, CT scan, or other imaging technique, or by a common preset anteversion angle. It should be appreciated by utilizing the instrument 200 and the trial 100, the proximal body 106 may be rotated with respect to the distal stem 102 an increment based on the index mechanism 120 of perhaps 10 degrees or less.

For example, the trial 100 may be preset utilizing instrument 200 to a particular first trial anteversion angle ααα. The trial 100 may then be inserted into a patient and a trial reduction performed. If the trial reduction indicates that the trial anteversion angle ααα should be increased or decreased, the nut may be loosened enough to permit rotation of the index mechanism 120 and the proper amount of change of anteversion can be set by utilizing the indicia 254 and the instrument 200, or by merely listening to clicks as the index mechanism 120 is indexed the appropriate number of teeth, with each tooth movement representing, for example, 10 degrees.

Figure 29:
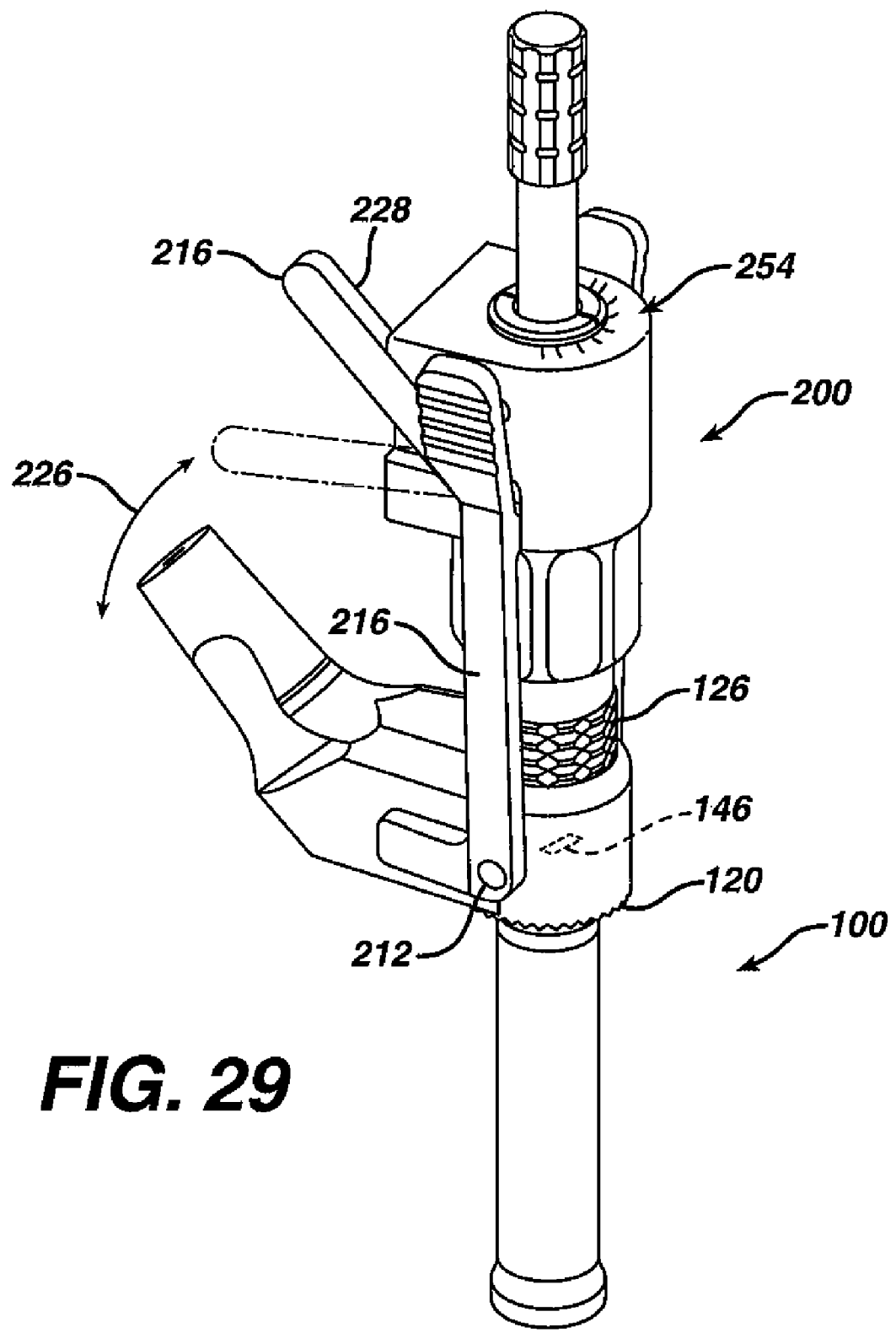
FIG. 29 is a partial perspective view of FIG. 27.
Figure 30:
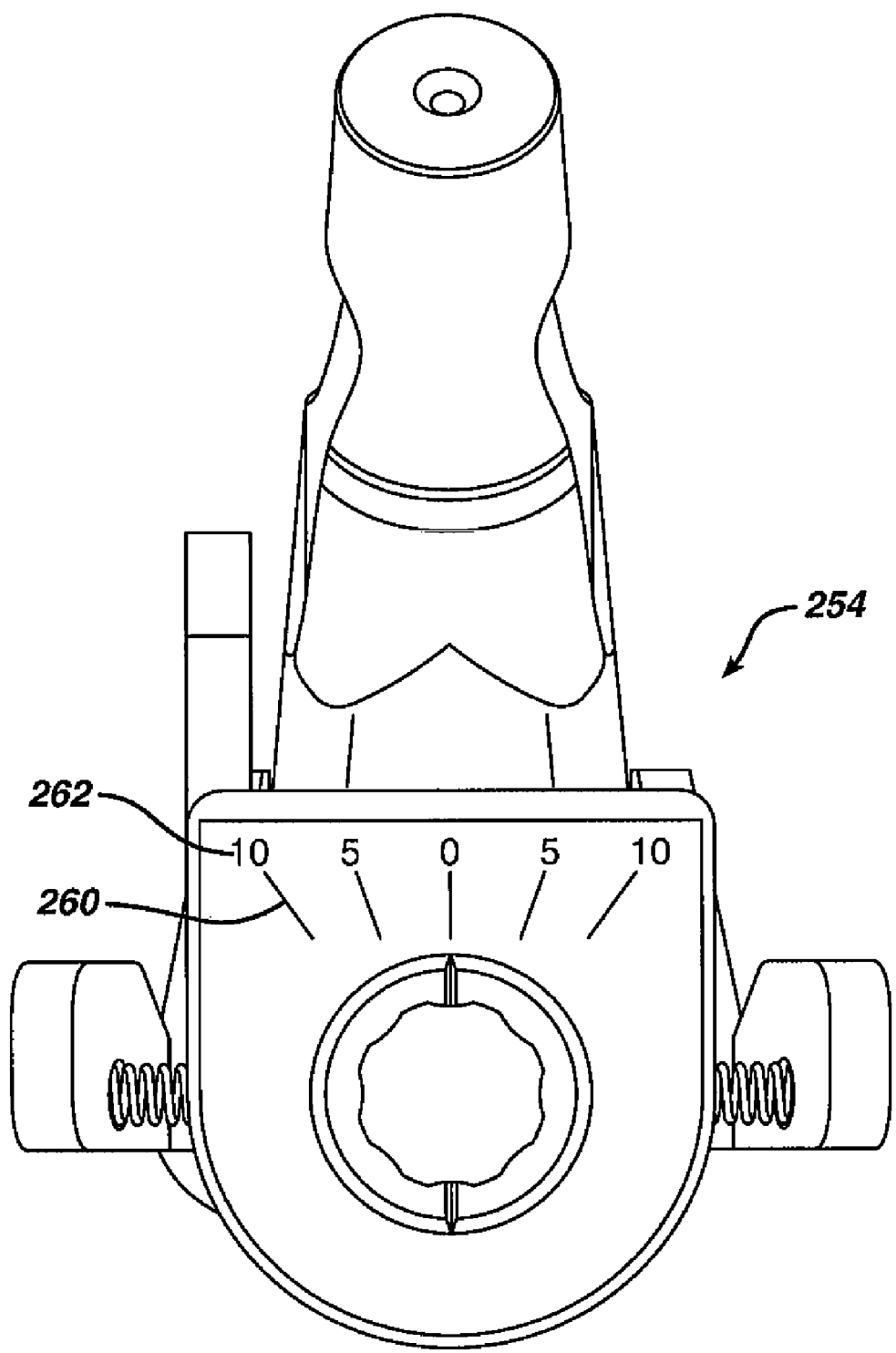
FIG. 30 is a top view of FIG. 27.

Referring now to FIGS. 29 and 30, once the ideal anteversion is determined for the use of the trial in the patient, the clinically proven correct anteversion can be measured by use of the instrument 200. Once the trial 100 is set in the proper position, the instrument 200 may be positioned into the trial 100 and the locking arms moved from its unlocked position (shown in solid in FIG. 29) to its locked position (shown in phantom in FIG. 29). Once the instrument 200 is locked in a desired setting, this desired setting may be repeated on, for example, an implant by reading the setting on the indicia 254 or by maintaining the instrument 200 in its locked position and utilizing the instrument to properly preset an implant or stem prosthesis.

Figure 31:
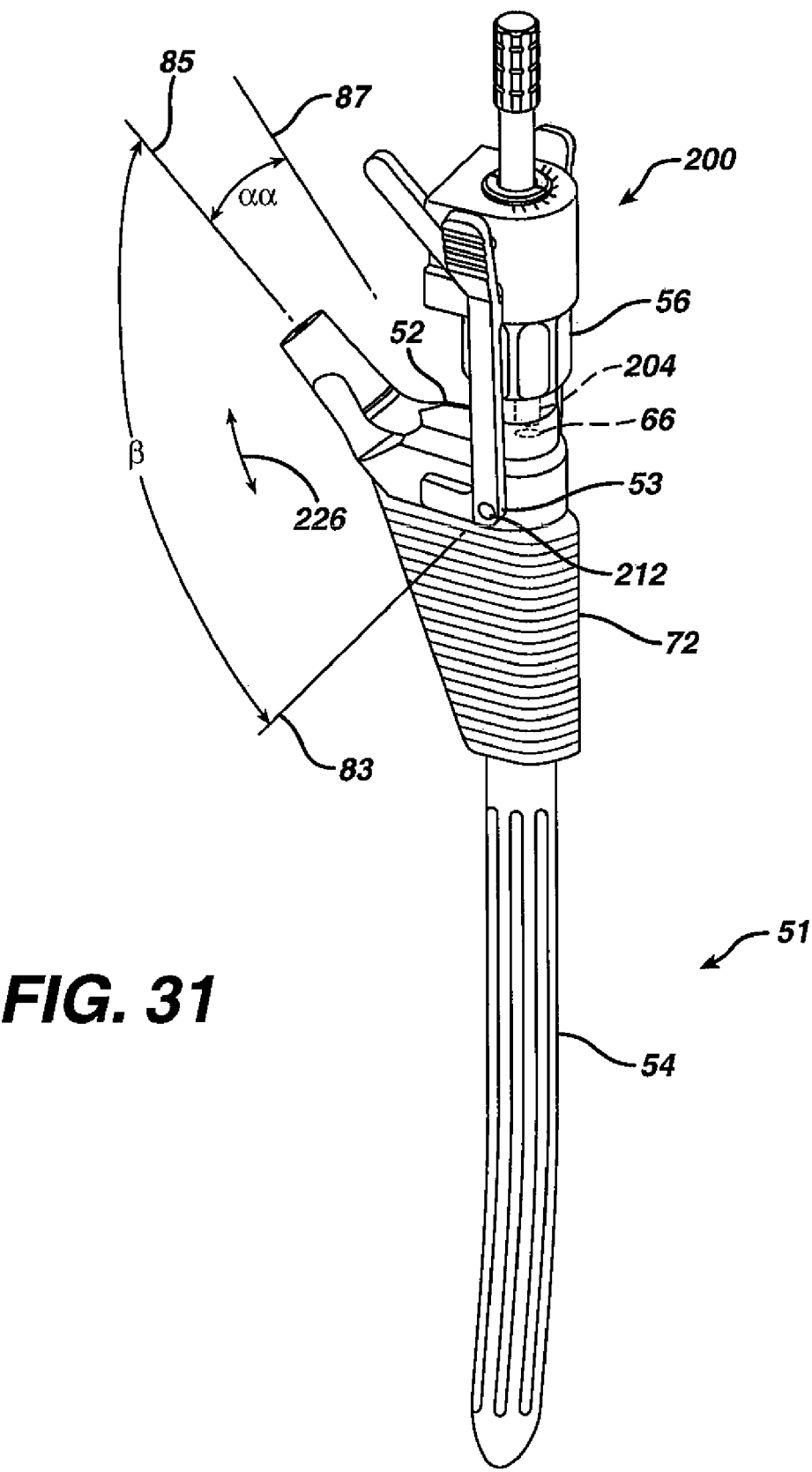
FIG. 31 is a perspective view of the alignment tool of FIG. 24 in position on the implant of FIG. 20.

Referring now to FIG. 31, the instrument 200 is shown in position on prosthetic hip stem 51. It should be appreciated that the instrument 200 may be similarly used on hip stems 10 of FIGS. 12 through 19. It should be appreciated that the trial 100 and the instrument 200 may also be used be used with monolithic stems. Once the proper anteversion is determined by the trial 100 and the instrument 200, a monolithic stem can be used with that determined anteversion.

Before the instrument 200 is installed onto the hip stem 51, the proximal body 52 is loosely fitted to the distal stem 54 so that the proximal body 52 may rotate in the direction of arrows 226 with respect to the distal stem 54. In this rotatable assembly condition of the hip stem 54, the instrument 200 is engaged with the hip stem 54. The proximal body 52 will be rotated in the direction of arrow 226 (see FIGS. 29 and 31) with respect to the distal stem 54 so that the key 204 may completely seat into the slot 66 of the distal stem 54 and so that the pin 212 may fully seat into the holes 53 in the hip proximal body 52. Once the instrument 200 is fully seated into the hip stem 54, the distal end of the distal stem 54 may be slightly tapped in an upward direction to seat the proximal body to hip stem 51.

Since the angle between the axis 83 of the pin 212 and the neck centerline 85, shown at β in FIG. 31, is fixed, and since the position of the axis 83 of the pin with respect to the hip stem 54 is set by the locked instrument 200, the implant can be fixed with the proper anteversion angle between the neck centerline 85 and a plane 87 through the anterior bow of the stem 56. In this secured and tapped position, the centerline neck centerline forms the prosthetic anteversion angle αα with the plane 87. Through the use of the instrument 200, the prosthetic anteversion angle αα is virtually identical to the trial anteversion angle ααα of the trial. (See FIG. 11) And since the plane 87 will correspond with the plane 29 through the anterior bow of the femur (See FIGS. 16 and 16A) when the prosthetic is implanted, proper orientation of the prosthetic head and neck can be achieved.

After the proximal body 52 has been seated temporarily into the distal stem 54, instrument 200 may be removed. After removal of the instrument 200, the proximal body 54 may be securely seated onto the distal stem 54 by utilizing tools (now shown) to finalize the assembly of the stem 51 and proximal body 52.

Figure 32:
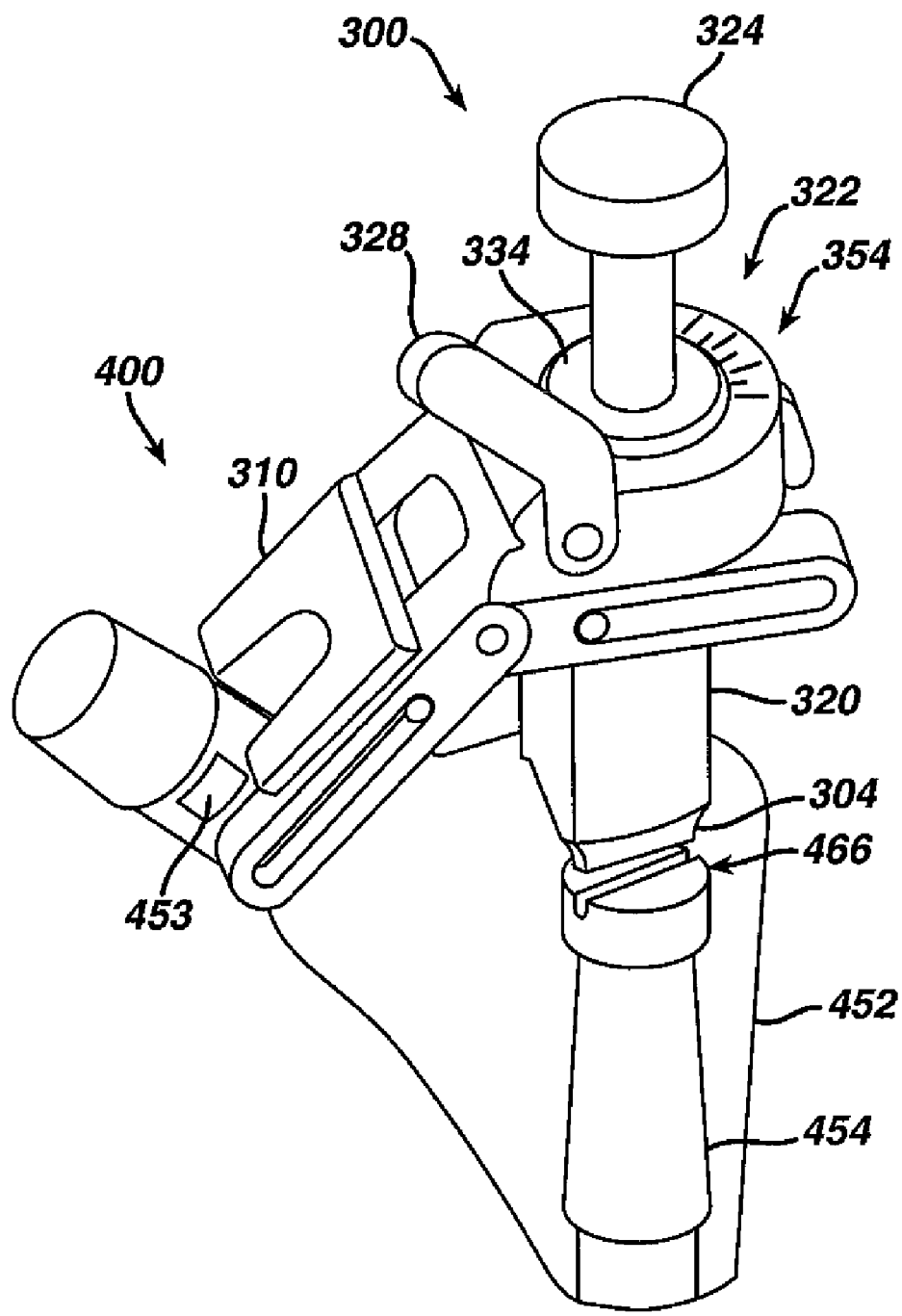
FIG. 32 is a perspective view of an alternate embodiment of an alignment tool that may be used to register the alignment of the modular trial of FIG. 1 or the hip stems of FIGS. 12 and 20 shown in position on the modular trial for registering the alignment the modular trial of FIG. 1.
Figure 33:
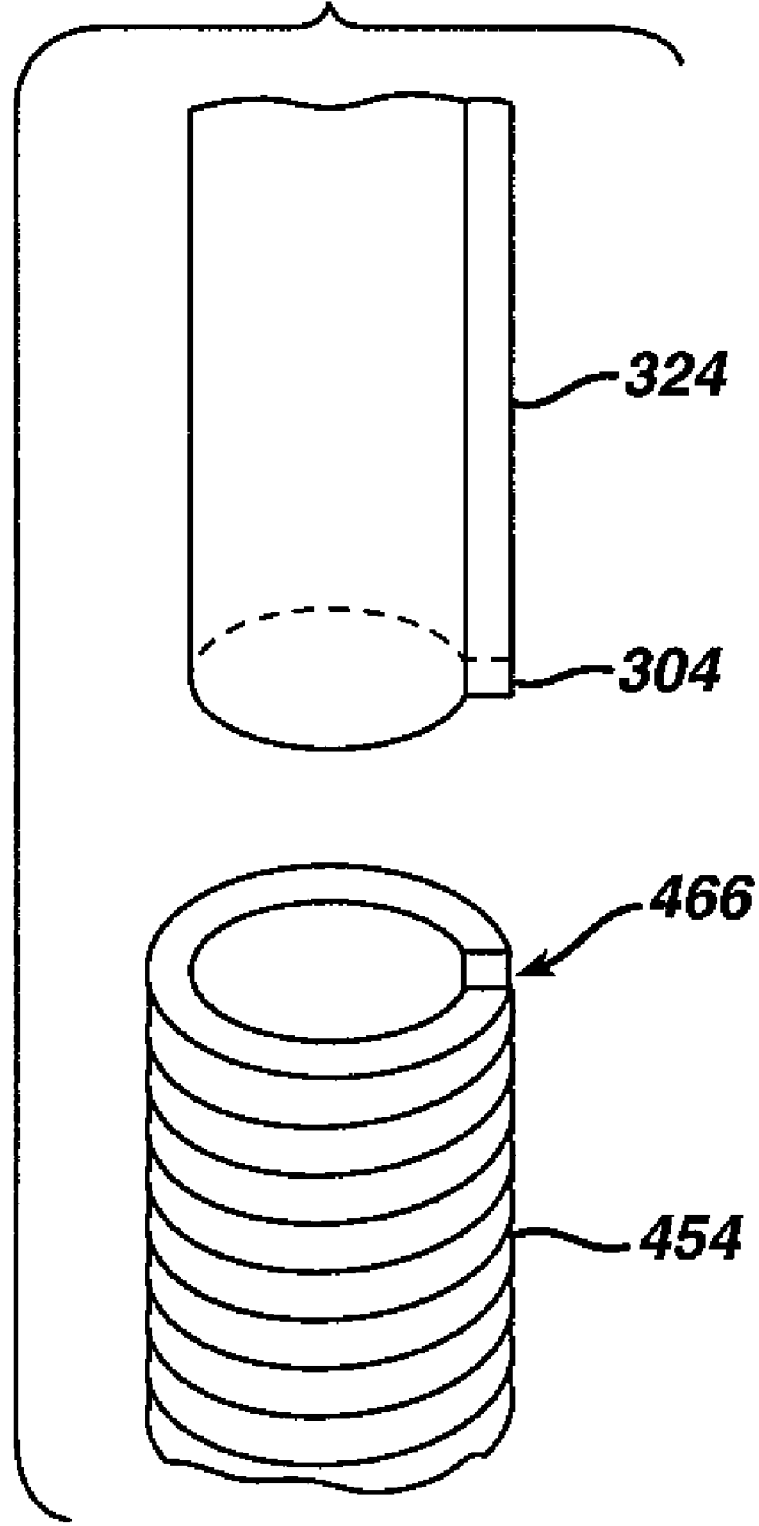
FIG. 33 is a partial perspective view of FIG. 32 showing the keyed timing of the distal stem of the trial with the alignment tool.

Referring now to FIGS. 32 and 33, an alternate orientation device is shown as orientation device 300. Orientation device 300 is similar to orientation device 200 of FIG. 24. The orientation device 300 includes a body 320 that defines an opening 322. Within the opening 322 is a sleeve 334. An orientation rod 324 is slidably fitted to the sleeve 334. A locking arm 328 selectively locks the sleeve 334 to the body 320. A tang 304 on the distal end of the orientation rod 324 may engage a slot 466 in the proximal end of the distal stem 454 of hip stem 400. An alignment fork 310 is slidably and rotatably fitted to the body 320. The alignment fork 310 engages the sides 453 of the neck 452 of hip stem 400. When utilizing the orientation device 300 the locking arm 328 may be positioned in an unlocked position and the tang 304 angularly adjusted with respect to alignment fork 310 until the alignment fork and the tang are properly seated into the proximal body 452 and the distal stem 454 of the hip stem 400, respectively.

Referring again to FIGS. 22 and 23, the orientation device 300 may include indicia 354 similar to the indicia 254 of the orientation device 200 of FIG. 24. The indicia 354 may include a single indicia located on sleeve 334 which cooperates with body indicia 360 on the body 320 to provide for a measurement of the anteversion of the hip stem 400.

Figure 34:
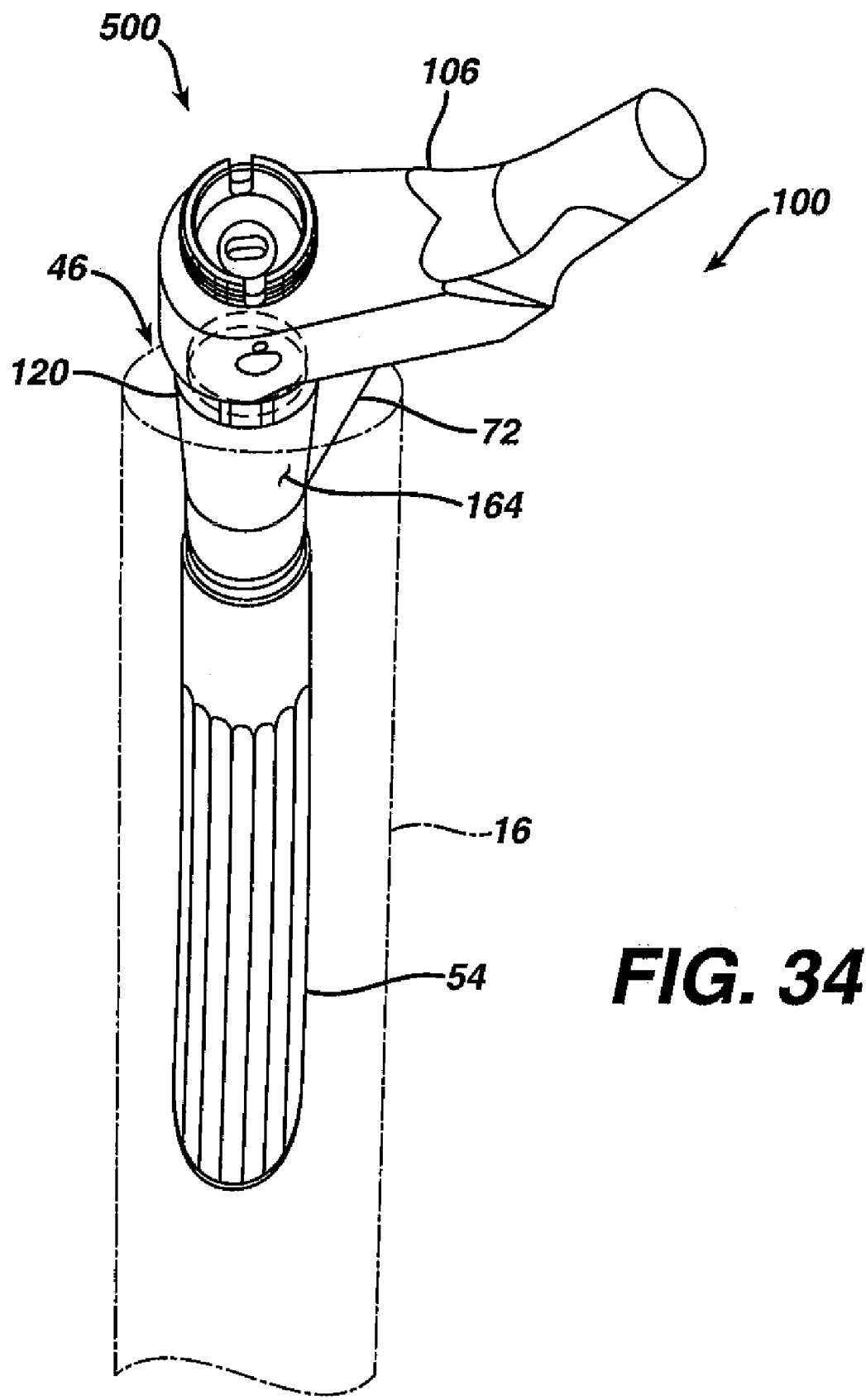
FIG. 34 is a perspective view of the distal stem of the modular hip stem of FIG. 20 in a femur with a neck and proximal body trial of FIG. 1.

Referring now to FIG. 34, another embodiment of the present invention is assembly 500. Assembly 500 is a combination of the neck trial 106 on the implant stem 54 of FIG. 1 including, for example, the index mechanism 120 and the inner sleeve 164 with distal stem 54 of the hip stem 51 of FIG. 20. As shown in FIG. 34, the surgeon may place a bowed distal stem 54 into the canal 46 of the long bone 16 and proximal body trial 164, a neck trial 106 may be placed on the distal stem implant 54. The instrument 200 of FIG. 24 may be placed on the assembly 500 to preset the anteversion angle prior to a trial reduction or the alignment device 200 utilized after a trial reduction has been performed utilizing the assembly 500 to determine the intraoperatively-found ideal anteversion angle so that it can be replicated with a proximal body implant. In this procedure, the proximal body implant would be placed on the distal stem 54 preferably utilizing the alignment tool 200 and once in proper position, the proximal body implant could be tapped in position. After being tapped into position, the alignment instrument 200 may be removed and a tool (not shown) may be used to secure the nut 56 to the distal stem 54 to secure the hip prosthesis 51 (See FIG. 21). It should be appreciated that a distal stem trial may likewise be used in conjunction with a proximal body implant. The distal stem trials may be smaller than the corresponding distal stem implants and thus may be used in conjunction with a proximal body implant to perform the trial reduction.

Figure 35:
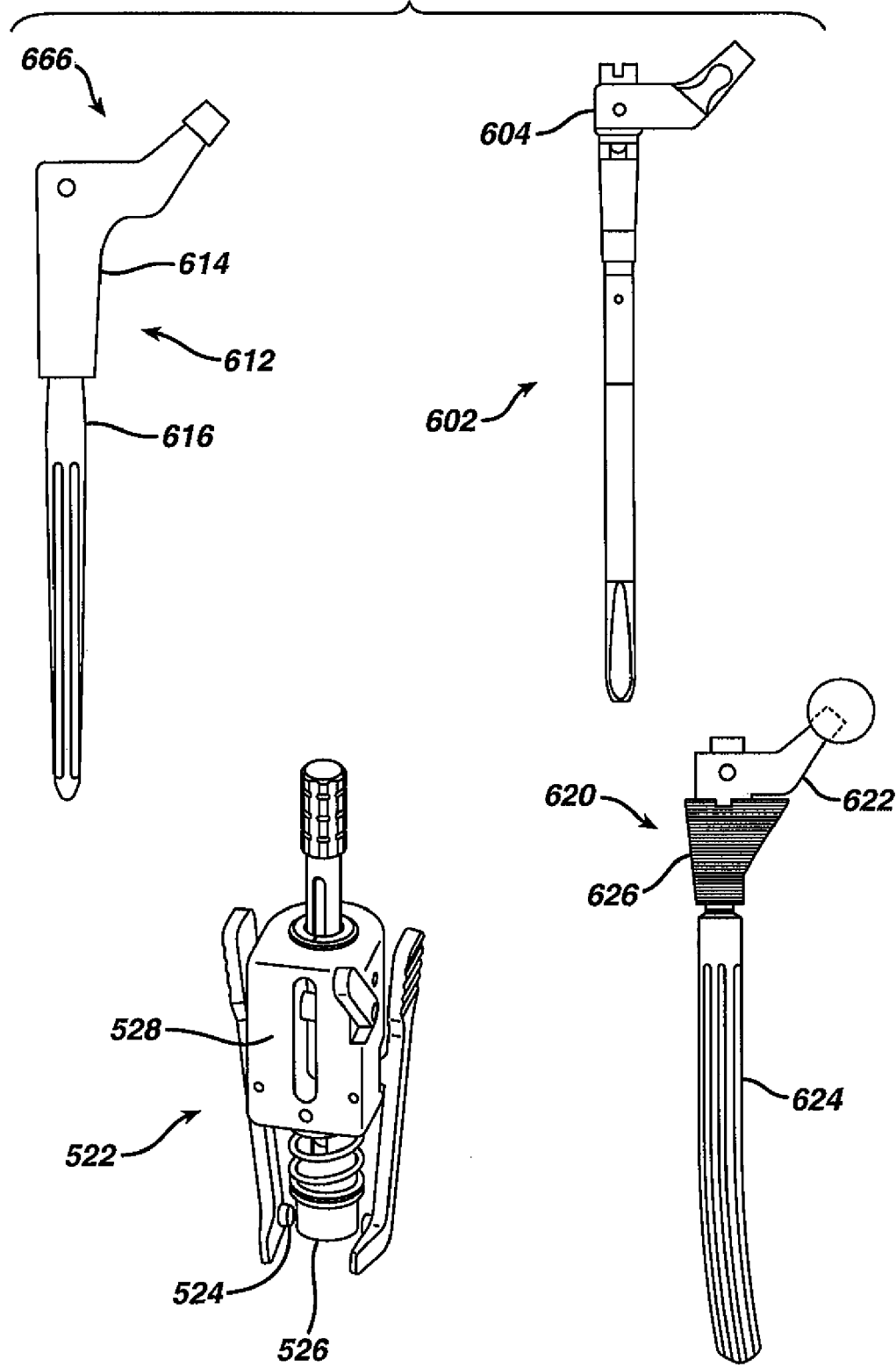
FIG. 35 is a plan and perspective view of a kit for use in arthroplasty according to the present invention.

Referring now to FIG. 35, a kit 666 according to the present invention is shown. The kit 666 is utilized to prepare a cavity in the femoral canal of a femur and to assist in performing a trial reduction. The kit 666 includes a trial 602 for use in performing joint arthroplasty. The trial 602 is to be fitted into a cavity in the canal of a long bone and to assist in performing a trial reduction in performing joint arthroplasty. The kit 666 may further include an instrument 522 for use in determining the selected position of the stem portion of a trial with respect to the neck portion of a trial and to determine the selected position of a stem component to a neck component of a prosthetic stem. The instrument 522 includes a first member 524 of cooperation with the neck component of a implant or a neck portion of a trial. The instrument 522 further includes second and third members 526 and 204 for cooperation with a stem portion of a trial and with a stem component of an implant. The instrument 522 further includes a body 528 for operatively interconnecting the first member 524 with the second member 526. The kit 666 may also include components for assembling one or more prosthetic components, such as the prosthetic femoral components shown at 612 and 620. Each of the prosthetic femoral components may include a proximal body 614, 624 and a distal stem 616, 624. Sleeves 626 could also be included in the kit 666.

Figure 36:
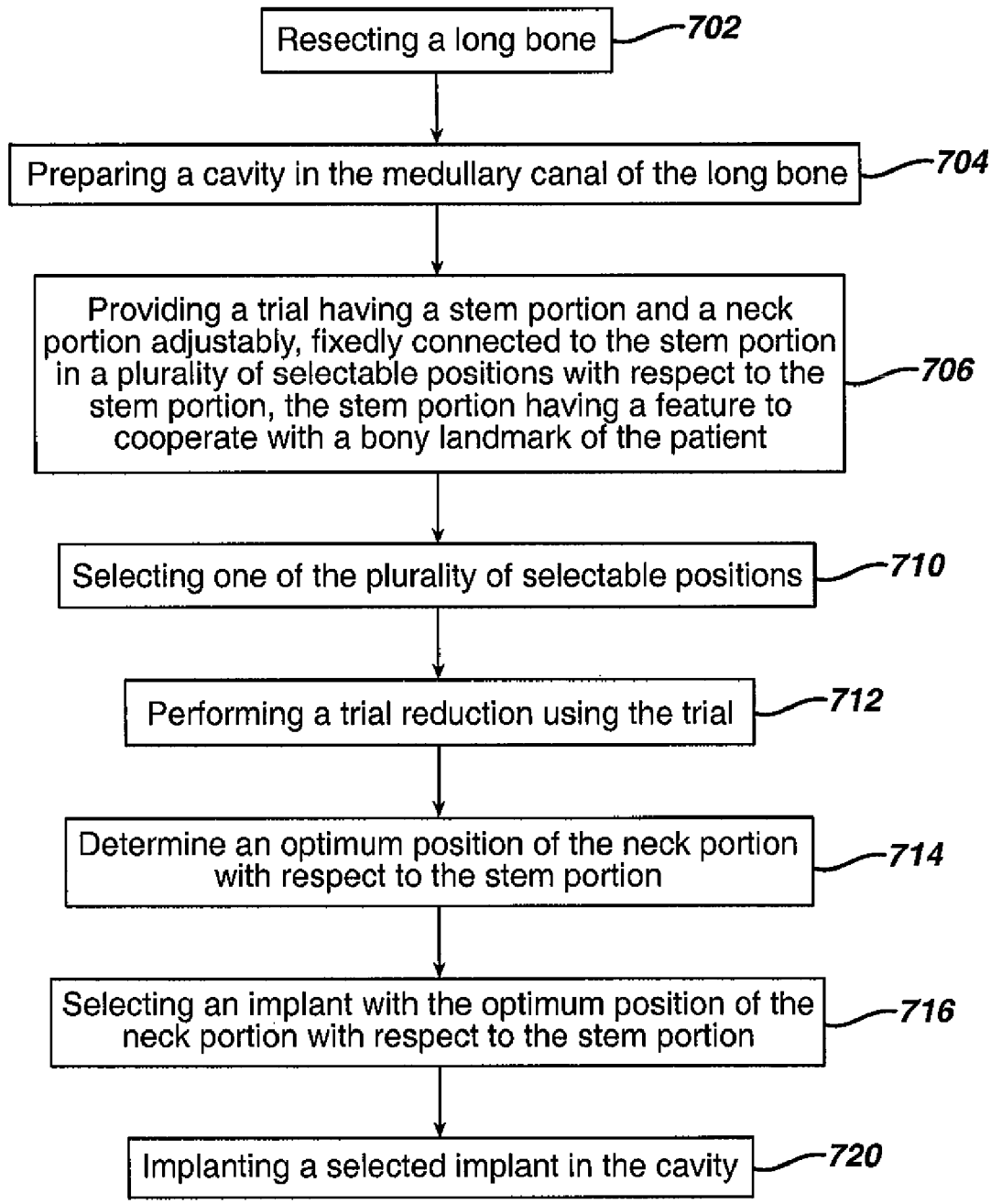
FIG. 36 is a process flow chart for a method of performing joint arthroplasty surgery according to an embodiment of the present invention.

Referring now to FIG. 36, a method for providing joint arthroplasty 700 is shown. The method 700 includes a step 702 of resecting a long bone. The method 700 further includes a step 704 of preparing a cavity in the medullary canal of a long bone. The method further includes the step 706 of providing a trial having a stem portion and neck portion adjustably fixably connected to the stem portion in a plurality of selectable positions with respect to the stem portion. The stem portion having a feature to cooperate with a bony landmark of the patient. The method further includes the step 710 of selecting one of a plurality of selectable positions of the trial. The method further includes step 712 of performing a trial reduction using the trial. The method further includes the step 714 of determining an optimal position of the neck portion with respect to the stem portion. The method further includes a step 716 of selecting an implant with the optimum position of the neck with respect to the stem as determined by the trial reduction. The method further includes the step 720 of implanting a selected implant into the cavity.

Although the present invention and its advantages have been described in detail, it should be understood that various changes, substitutions, and alterations can be made therein without departing from the spirit and scope of the present invention as defined by the appended claims.

We claim:

1. A kit for use in performing joint arthroplasty, said kit comprising:

a trial for use in performing joint arthroplasty, said trial to be fitted to a cavity in the canal of a long bone and to assist in performing a trial reduction in performing joint arthroplasty, said trial including a stem portion and a neck portion selectively operably connected to said stem portion in at least three discrete spaced apart positions with respect to said stem portion;

an implant for use in performing joint arthroplasty, said implant to be fitted to a cavity in the canal of a long bone and to assist in performing joint arthroplasty, said implant including a stem portion and a proximal body portion selectively operably connected to said stem portion in at least three discrete spaced apart positions with respect to said stem portion; and an alignment device for replicating the alignment of said trial onto said implant, said alignment device adapted to be fitted to said trial at one of said three discrete spaced apart positions and adapted to be fitted to said implant at a corresponding one of said three discrete spaced apart positions, wherein the alignment device includes a first member and a second member that is movable relative to the first member, the alignment device further including a body coupled to the first and second members for at least one of replicating and measuring the relative angular orientation of the stem portion relative to the neck portion, the body further comprising a lock for selectively preventing relative motion between the first member and the second member.

2. The kit of claim 1, wherein said stem portion comprises a distal stem and a proximal body, said distal stem and proximal body are discrete components and said stem portion comprises an assembly of said discrete components, said proximal body comprises an assembly including a keyed member, spline member, ring and sleeve.

3. The kit of claim 1, wherein said stem portion has an elongated arcuate rod shaped external periphery, the arcuate rod shaped external periphery conforming to the medullary canal of the femur.

4. The kit of claim 1:
wherein said stem portion defines a longitudinal axis thereof;
wherein said neck portion defines an opening therein, the opening defining a longitudinal axis thereof, the longitudinal axis of the opening being coincident with the longitudinal axis of said stem portion; and
wherein said neck portion is rotatably connected to said stem portion about the longitudinal axis of said stem portion.

5. The kit of claim 1, further including a sleeve rotatably positioned on the outer periphery of said stem portion.

6. The kit of claim 1:
further comprising a locating feature associated with said stem portion;
wherein said neck portion comprises a second locating feature; and
wherein both locating features are accessible from the proximal end of the trial.

7. The kit of claim 1, wherein said neck portion is fixedly connected to said stem portion by means of an indexing mechanism providing the at least three spaced apart discrete angular positions of said neck portion with respect to said stem portion.

8. The kit of claim 1, further comprising a resilient connector for connecting said neck portion to said stem portion, said connection including a first set of teeth operably connected to said neck component, a second set of teeth operably connected to said stem component, said first set of teeth and second set of teeth adapted for indexable engagement with each other to provide for a plurality of discrete spaced apart angular positions of said neck component with respect to said stem component, and a spring for biasing said first set of teeth into engagement with said second set of teeth.

* * * * *